US009933428B2

(12) United States Patent
Chan et al.

(10) Patent No.: US 9,933,428 B2
(45) Date of Patent: Apr. 3, 2018

(54) IMMUNOASSAY TEST SLIDE

(71) Applicant: IDEXX Laboratories, Inc., Westbrook, ME (US)

(72) Inventors: Eugene Chan, Portland, ME (US); Keith Nassif, Saco, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 796 days.

(21) Appl. No.: 14/358,280

(22) PCT Filed: Jan. 7, 2013

(86) PCT No.: PCT/US2013/020483
§ 371 (c)(1),
(2) Date: May 15, 2014

(87) PCT Pub. No.: WO2013/106269
PCT Pub. Date: Jul. 18, 2013

(65) Prior Publication Data
US 2014/0315216 A1 Oct. 23, 2014

Related U.S. Application Data

(60) Provisional application No. 61/585,050, filed on Jan. 10, 2012.

(51) Int. Cl.
*G01N 33/557* (2006.01)
*G01N 33/573* (2006.01)
*G01N 35/00* (2006.01)
*G01N 33/543* (2006.01)

(52) U.S. Cl.
CPC ..... *G01N 33/573* (2013.01); *G01N 33/54366* (2013.01); *G01N 35/00029* (2013.01); *G01N 2035/00138* (2013.01); *G01N 2333/918* (2013.01)

(58) Field of Classification Search
None
See application file for complete search history.

(56) References Cited

U.S. PATENT DOCUMENTS

| 4,387,990 | A | 6/1983 | Yazawa et al. ............... 356/244 |
| 5,089,229 | A | 2/1992 | Heidt et al. ..................... 422/64 |
| 5,185,127 | A | 2/1993 | Vonk .............................. 422/56 |
| 5,376,551 | A | 12/1994 | Yoshikami ..................... 436/56 |
| 5,552,276 | A | 9/1996 | Mochida et al. ................. 435/6 |
| 5,597,532 | A | 1/1997 | Connolly ........................ 422/58 |
| 5,726,010 | A | 3/1998 | Clark ............................... 435/5 |
| 5,726,013 | A | 3/1998 | Clark ............................... 435/5 |
| 5,750,333 | A | 5/1998 | Clark ............................... 435/5 |
| 5,770,441 | A * | 6/1998 | Lipton .................. C12M 23/04 435/289.1 |
| 5,807,751 | A | 9/1998 | Alajem et al. ................ 436/501 |
| 6,235,241 | B1 | 5/2001 | Catt et al. ....................... 422/56 |
| 6,399,398 | B1 | 6/2002 | Cunningham et al. ....... 436/534 |
| 7,816,122 | B2 | 10/2010 | Clark et al. ................. 435/287.1 |
| 8,475,735 | B2 | 7/2013 | Babu et al. .................... 422/420 |
| 2001/0039057 | A1 | 11/2001 | Douglas et al. .............. 436/169 |
| 2002/0025278 | A1* | 2/2002 | Anderson ........ G01N 27/44704 422/400 |
| 2002/0057991 | A1* | 5/2002 | Kelly ........................ B01L 3/50 422/408 |
| 2003/0129767 | A1 | 7/2003 | Bautista et al. .............. 436/178 |
| 2003/0170768 | A1 | 9/2003 | Anaokar et al. ................ 435/19 |
| 2004/0137640 | A1 | 7/2004 | Hirao et al. ................... 436/514 |
| 2004/0171173 | A1 | 9/2004 | Eckermann et al. ......... 436/514 |

(Continued)

FOREIGN PATENT DOCUMENTS

| CN | 201449486 | 5/2010 | ............. G02B 21/34 |
| CN | 201540288 | 8/2010 | ............. G01N 21/31 |

(Continued)

OTHER PUBLICATIONS

Notification of Transmittal of the International Search Report dated Mar. 22, 2013, the International Search Report dated Mar. 22, 2013 and the Written Opinion of the International Searching Authority, in English, dated Mar. 22, 2013, issued from WIPO for Applicant's corresponding PCT Application No. PCT/US13/20483, filed on Jan. 7, 2013.

Supplementary Partial European Search Report and Annex to the European Search Report, in English, dated Jul. 1, 2015, issued from the European Patent Office for Applicant's corresponding European Patent Application No. 13736046.7, filed on Jan. 7, 2013.

Chinese First Office Action (in Chinese and English), dated Jun. 26, 2015, Text of First Office Action and Search Report (in English), dated Jun. 15, 2015, which issued from the State Intellectual Property Office of People's Republic of China for Applicant's corresponding Chinese Application No. 201380005166.6, filed on Jan. 7, 2013.

Japanese Office Action (in Japanese) with English translation, dated Nov. 15, 2016, which issued from the Japanese Patent Office for Applicant's corresponding Japanese Application No. 2014-552226, filed on Jul. 9, 2014.

*Primary Examiner* — Ann Lam
(74) *Attorney, Agent, or Firm* — Bodner & O'Rourke, LLP; Gerald T. Bodner; Christian P. Bodner

(57) ABSTRACT

An immunoassay test slide for use in a dry chemistry analytical instrument includes a slide housing or case formed from two matable sections—a slide cover piece and a slide bottom piece. The slide housing defines an interior cavity in which is situated a sheet-like porous carrier matrix. The slide cover piece has an opening formed through the thickness thereof to expose a central portion of the fluid flow matrix so that a precise volume of fluid sample of blood, serum or the like, preferably pre-mixed with a conjugate reagent, and precise volumes of a wash reagent and a substrate (detector reagent), may be deposited on the matrix through the cover opening by a metering device of the analytical instrument. The bottom piece of the immunoassay test slide is transparent, and the slide is moved by a transport mechanism of the analytical instrument over a reflectometer or a fluorometer for performing reflectance or fluorescence measurements.

47 Claims, 23 Drawing Sheets

(56) References Cited

U.S. PATENT DOCUMENTS

| | | | | |
|---|---|---|---|---|
| 2004/0178073 A1* | 9/2004 | Kozulic | ............. | G01N 27/4473 204/462 |
| 2006/0109475 A1* | 5/2006 | Misener | ............... | G01N 21/474 356/446 |
| 2006/0257999 A1* | 11/2006 | Chang | ................. | B01J 19/0046 435/289.1 |
| 2006/0263907 A1* | 11/2006 | Zweig | ................... | B82Y 15/00 436/524 |
| 2007/0032622 A1* | 2/2007 | Barfurth | ................... | C07F 7/21 528/10 |
| 2007/0087357 A1 | 4/2007 | Clark et al. | ........................ | 435/6 |
| 2007/0092401 A1 | 4/2007 | Liao et al. | ...................... | 422/58 |
| 2008/0199851 A1* | 8/2008 | Egan | .................... | B01L 3/5023 435/5 |
| 2010/0066543 A1 | 3/2010 | Drucker et al. | ........... | 340/573.1 |
| 2010/0126862 A1* | 5/2010 | Sabin | ................... | G01N 27/447 204/457 |
| 2010/0129789 A1 | 5/2010 | Self et al. | ......................... | 435/5 |
| 2010/0254854 A1 | 10/2010 | Rich et al. | ...................... | 422/64 |
| 2011/0062024 A1* | 3/2011 | Sabin | .............. | G01N 27/44791 204/457 |
| 2011/0071036 A1* | 3/2011 | Penterman | ........ | G01N 27/44791 506/7 |
| 2012/0270235 A1* | 10/2012 | Kim | ..................... | G01N 33/538 435/7.9 |
| 2013/0023444 A1* | 1/2013 | Kovalenko | .............. | C12Q 1/28 506/12 |

FOREIGN PATENT DOCUMENTS

| | | | |
|---|---|---|---|
| EP | 1 114 997 | 7/2001 | ............. G01N 33/49 |
| JP | S56-142454 | 10/1981 | ............. G01N 21/01 |
| JP | H03-118473 | 5/1991 | ............... B01N 3/00 |
| JP | H06-273419 | 9/1994 | .......... G01N 33/543 |
| JP | H07-191020 | 7/1995 | ............. G01N 21/78 |
| JP | H10-505909 | 6/1998 | ................ G01N 1/10 |
| JP | H10-274624 | 10/1998 | ................ B01L 3/00 |
| JP | 2006-098229 | 4/2006 | ............. G01N 21/01 |
| JP | 2008-518215 | 5/2008 | ............. G01N 33/53 |
| WO | WO 96/09546 | 3/1996 | ................ G01N 1/10 |
| WO | WO 99/23475 | 5/1999 | ............. G01N 21/64 |
| WO | WO 99/23475 A1 | 5/1999 | |
| WO | WO 2006/105110 | 10/2006 | ............. C12M 3/00 |
| WO | WO 2008/140742 | 11/2008 | ............. G01N 21/00 |
| WO | WO 2008/140742 A1 | 11/2008 | |
| WO | WO 2011/124991 | 10/2011 | ................ B01L 3/00 |

* cited by examiner

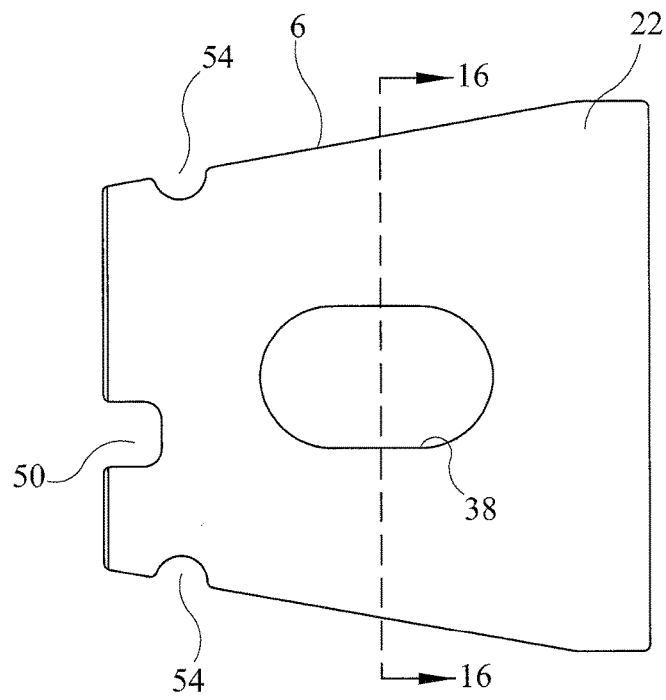
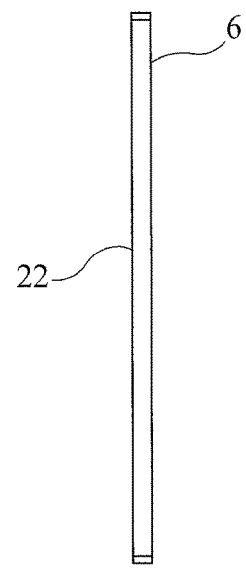
FIG. 13        FIG. 15
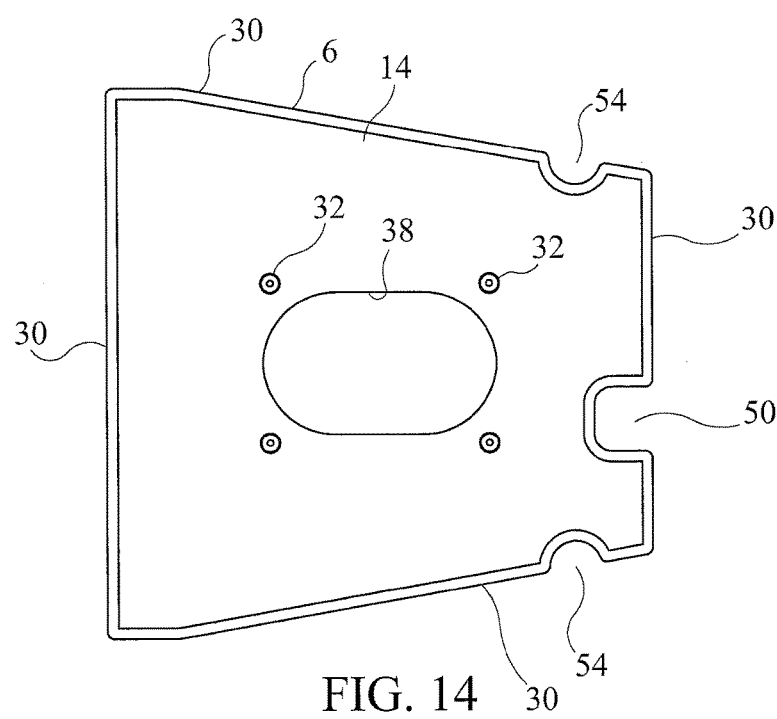
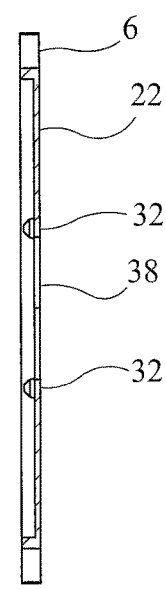
FIG. 14        FIG. 16

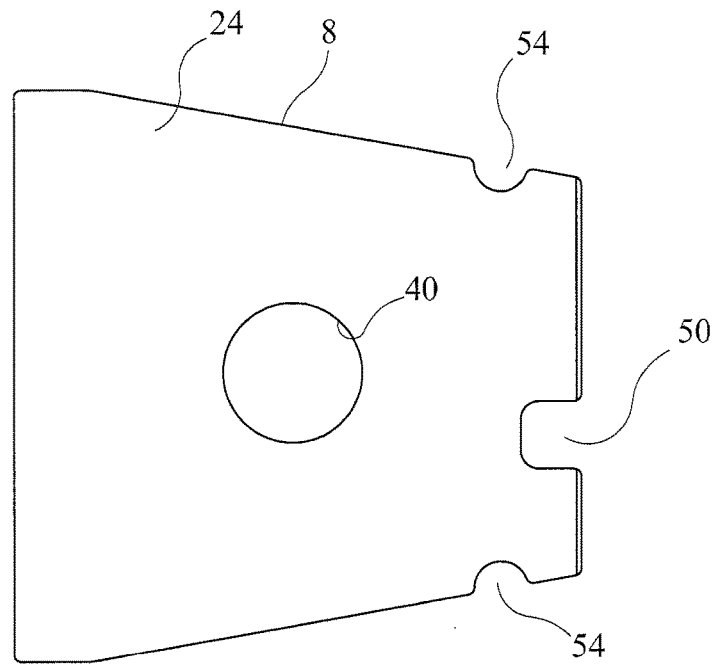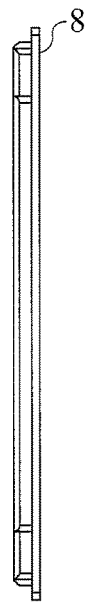
FIG. 17  FIG. 19
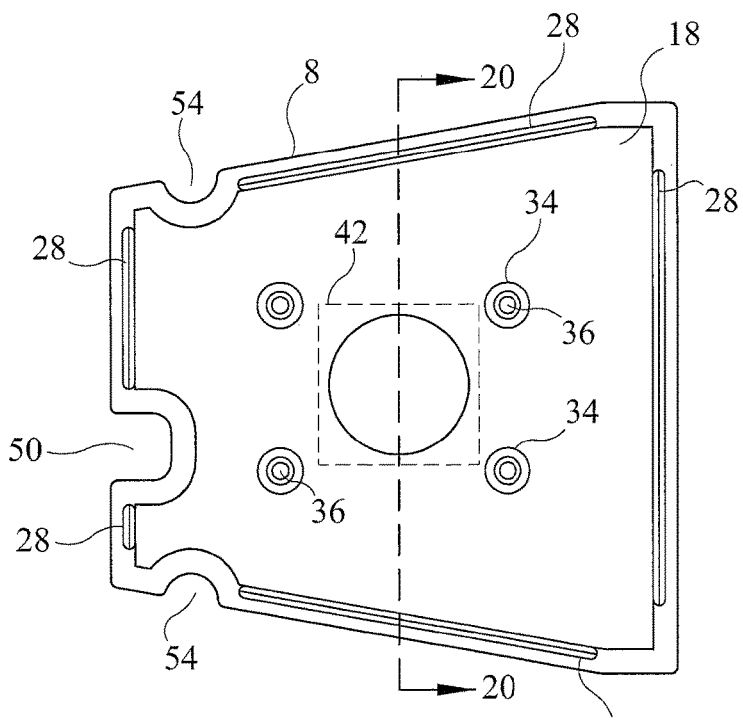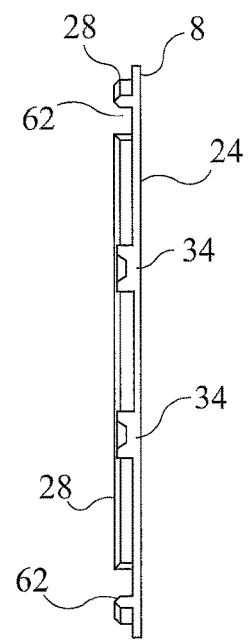
FIG. 18  FIG. 20

IMMUNOASSAY TEST SLIDE

CROSS-REFERENCE TO RELATED APPLICATIONS

This application is related to U.S. Provisional Application Ser. No. 61/585,050, filed on Jan. 10, 2012, and entitled "Immunoassay Test Slide", the disclosure of which is incorporated herein by reference and on which priority is hereby claimed.

BACKGROUND OF THE INVENTION

Field of the Invention

The present invention relates to devices and methods for performing assays to determine the presence or quantity of a specific analyte of interest in a fluid sample.

Description of the Prior Art

Many devices for the detection and/or quantification of an analyte of interest in a fluid sample are well known and are the lateral-flow type or micro-well type. Generally, lateral flow devices include a solid phase fluid permeable flow path through which a sample and various reagents travel by capillary action. The flow path has immobilized thereon various binding reagents for the analyte (or analog thereof), other binding partners, or conjugates involving binding partners for the analyte and members of signal producing systems (e.g., a label). The various assay formats used with these devices are well known for the direct or indirect detection of the analyte of interest in the test sample.m U.S. Pat. Nos. 5,726,010, 5,726,013, 5,750,333 and 7,816,122, each of which issued to Scott M. Clark and which are assigned of record to IDEXX Laboratories, Inc., the disclosures of which are incorporated herein by reference, describe assay methods and devices that use the formation of a solid phase bound tertiary complex to detect an analyte of interest in a fluid sample. The devices disclosed in the Clark patents utilize a reversible flow in a chromatographic binding assay. An analyte-containing solution is applied to the device and then is transported by capillary action, first in one direction and then in the opposite direction, along an elongated flow matrix. The flow matrix generally includes four different regions. Region one is where a solution having the sample mixed with either a labeled antibody or antigen is added. Region two, also called the detection zone, contains the second antibody or antigen, which is immobilized to a solid phase. Region three contains a site to apply a wash solution. Region four contains an absorbent reservoir located near region one and makes the flow go in the opposite direction. The device also includes means to detect the presence or quantity of an analyte.

The reversible lateral flow device disclosed in the Clark patents works quite well in detecting an analyte in a fluid sample. However, it, like other lateral flow devices, requires relatively significant sample volume and other reagents so that the matrix can be sufficiently wetted to allow for lateral flow of the sample liquid, wash and substrate. More specifically, such lateral flow devices may require approximately 0.35 grams (0.35 milliliters) of the sample liquid. Thus, samples often need to be diluted when sample volumes are small.

Dry chemical reagent test slides having a film surrounded by a frame are also well known in the art and are used to analyze a blood or fluid sample deposited thereon in a chemical analyzer, such as disclosed in U.S. Pat. No. 5,089,229 (Heidt, et al.) and U.S. Patent Application Publication No. 2010/0254854 (Rich, et al.), the disclosures of which are incorporated herein by reference. The sample deposited on the slides reacts with the chemical reagent on the film, and the reflectance or fluorescence of the slides is then measured by the chemical analyzer to detect a compound or substance found in the sample, such as calcium (Ca), aspartate transaminase (AST) or glucose (Glu), which could be an indication of a condition or disease. Only small aliquots of sample fluid need be deposited on the slides for detection of certain indicators of diseases. It would be advantageous if immunoassays could be performed on such dry chemistry analytical instruments using test slides.

OBJECTS AND SUMMARY OF THE INVENTION

It is an object of the present invention to provide an immunoassay test slide formed in accordance with the present invention which may be used in a dry chemistry analytical instrument.

It is another object of the present invention to provide a method in accordance with the present invention for manufacturing such an immunoassay slide.

It is a further object of the present invention to provide a method in accordance with the present invention for performing assays in a dry chemistry analytical instrument using the immunoassay test slide of the present invention.

In accordance with one form of the present invention, an immunoassay test slide for use in a dry chemistry analytical instrument, and for performing assays for detecting the presence or quantity of an analyte (e.g., an antigen or antibody, and the like), includes a slide housing or case formed from two matable sections—a generally planar slide cover piece and a generally planar slide bottom piece joinable to the cover piece. The slide housing formed from the cover piece and bottom piece, when joined together, is substantially leakproof during use and defines an interior cavity. A sheet-like porous carrier matrix is disposed within the confines of the housing cavity.

The slide cover piece has an opening formed through the thickness thereof to expose a central portion of the fluid flow matrix. The opening in the cover piece is provided to expose a central portion of the porous carrier matrix so that a precise volume of fluid sample (e.g., blood, serum and the like), preferably pre-mixed with a conjugate reagent, as will be explained, a wash reagent and a substrate (detector reagent), may be deposited on the matrix through the cover opening by a metering device of the analytical instrument. The central portion of the carrier matrix has deposited thereon a dried and immobilized specific binding reagent situated in alignment with the central opening in the cover piece.

The bottom piece of the immunoassay test slide also includes a central opening formed through the thickness thereof, which opening may be covered by a thin sheet of transparent (clear) material, such as Mylar, to avoid contamination and maintain the leakproofness of the housing. The opening in the bottom piece is provided so that reflectance or fluorescence measurements may be made of the immunoassay slide as it is transported by the analytical instrument over a reflectometer or fluorometer forming part of the analytical instrument. Alternatively, the bottom piece of the immunoassay test slide may be formed of a transparent material, in lieu of having the opening formed in the bottom piece, in order to conduct such measurements on the slide.

The overall shape of immunoassay test slide is preferably either rectangular or square, similar to the chemical reagent test slides disclosed in the aforementioned Heidt, et al. '229 patent (U.S. Pat. No. 5,089,229), or trapezoidal, similar to the chemical reagent test slides disclosed in the aforementioned Rich, et al. published application (Publication No. 2010/0254854). The thickness of the immunoassay test slide is preferably the same as or slightly greater than that of conventional dry chemistry slides so that they may be useable with existing dry chemistry analytical instruments which accept such dry chemistry slides, as disclosed in the aforementioned Heidt, et al. patent and Rich, et al. published application.

In accordance with a method of using the immunoassay test slide on a dry chemistry analytical instrument to perform an assay, the immunoassay test slide is loaded into a transport mechanism of the analytical instrument, which moves the slide under a sample metering device and above a reflectometer or fluorometer. An aliquot of fluid sample contained in a vial is also loaded into the analytical instrument. The fluid sample may have been pre-mixed with a conjugate reagent prior to being loaded into the analytical instrument, or mixed with the conjugate reagent by the instrument. Depending upon the assay format, the conjugate reagent may specifically bind to an analyte in the fluid sample to form a complex of the analyte and the conjugate reagent. In another aspect, the conjugate reagent includes an analyte analog, which does not complex with the analyte. The sample/conjugate reagent mixture is then incubated for a predetermined period of time.

Then, a predetermined volume of sample/conjugate is metered onto the immunoassay test slide through the opening formed in the cover piece by the metering device of the analytical instrument. The sample liquid containing the analyte and the conjugate reagent, whether complexed or not, flows into the central portion of the matrix located at the top opening in the cover piece and is transported by capillary action in all directions within the matrix. After that, a series of washes of the test slide is performed by having the metering device of the analytical instrument deposit predetermined volumes of a wash reagent on to the slide through the top opening of the cover piece. Finally, a predetermined volume of a substrate, such as a detector reagent, is added to the slide through the top opening by the metering device of the analytical instrument.

Reflectance or fluorescence measurements are then taken of the slide through the clear bottom piece or bottom opening of the slide at a particular wavelength. The presence or quantity of a specific analyte of interest in the fluid sample may be determined by such measurements. Preferably, there is a detectable color reaction on the slide which is measured by the analytical instrument that is used in the detection and quantification of the analyte in the fluid sample.

The immunoassay test slide of the present invention may be formed by placing a die cut section of porous carrier matrix from a sheet of the same material between a cover piece and a bottom piece of a plastic material, such as polystyrene, specifically shaped to be matable. The two pieces may be joined together by applying heat or an adhesive to define a substantially leakproof housing in which resides the porous carrier matrix. The porous carrier matrix may be spotted with an immobilized specific binding reagent prior to its insertion between the two mating slide pieces, or may be spotted with the specific binding reagent and heated to a specific temperature and for a predetermined period time to dry and immobilize the binding reagent in the central portion of the matrix under the opening in the cover piece. If a bottom opening, framed in the bottom piece of the immunoassay test slide, is provided, then prior to the insertion of the porous carrier matrix between the cover piece and the bottom piece, a thin sheet of transparent (clear) material, such as Mylar, is placed within the interior cavity defined by the slide housing over the bottom opening. Alternatively, no such bottom opening or covering sheet is required if the bottom piece of the slide is formed from a light transmissible or transparent material.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 13 is a plan view of the outer side of a cover piece of an immunoassay test slide formed in accordance with the present invention.

FIG. 14 is a plan view of the inner side of the cover piece of the immunoassay test slide formed in accordance with the present invention.

FIG. 15 is a side view of the cover piece of the immunoassay test slide of formed in accordance with the present invention.

FIG. 16 is a cross-sectional view of the cover piece of the immunoassay test slide of the present invention taken along line 16-16 of FIG. 14.

FIG. 17 is a plan view of the outer side of a bottom piece of an immunoassay test slide formed in accordance with the present invention.

FIG. 18 is a plan view of an inner side of the bottom piece of the immunoassay test slide formed in accordance with the present invention.

FIG. 19 is a side view of the bottom piece of the immunoassay test slide formed in accordance with the present invention.

FIG. 20 is a cross-sectional view of the bottom piece of the immunoassay test slide of the present invention taken along line 20-20 of FIG. 18.

FIG. 28 is a front isometric view of the chemical analyzer of the present invention shown in FIG. 22, and illustrating the extension from the front face of the analyzer housing of a tray for carrying a diluent and mixing cup or other cups for containing reagents and the like.

DETAILED DESCRIPTION OF THE PREFERRED EMBODIMENTS

Figure 1:
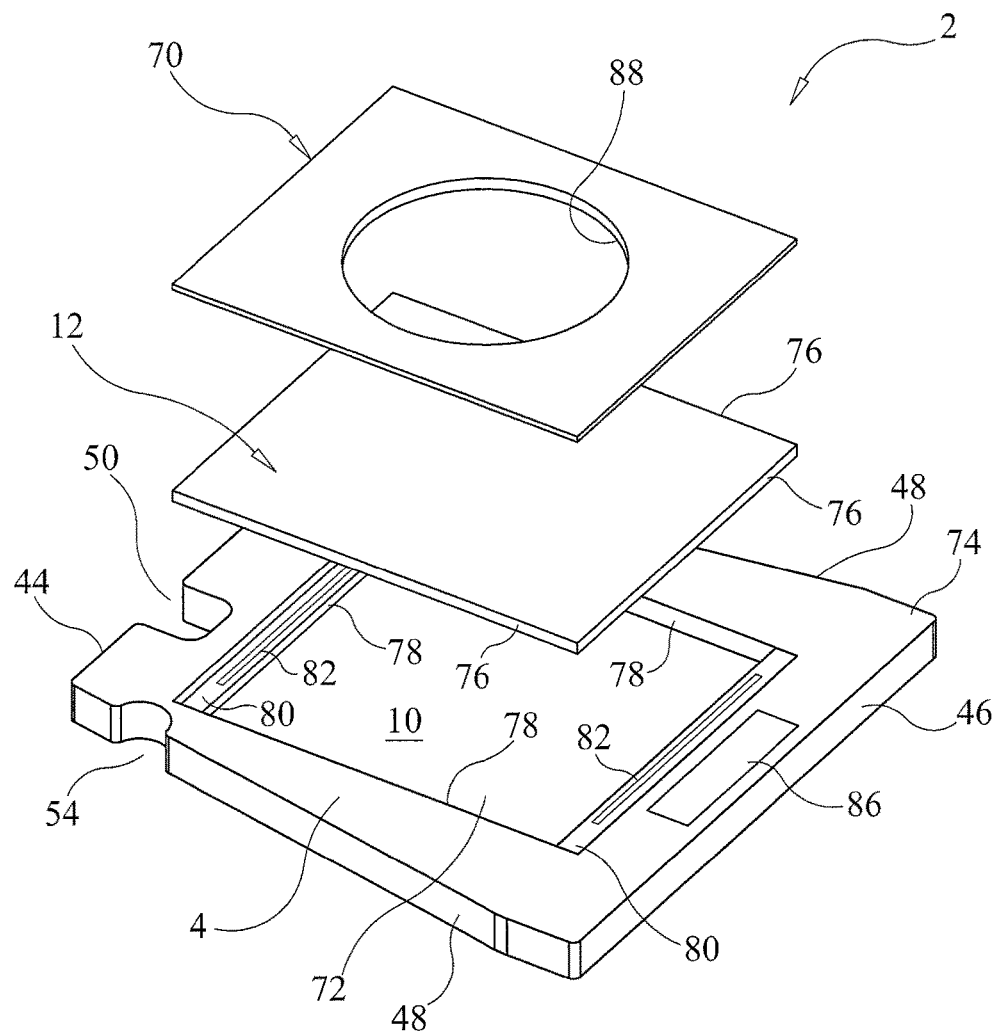
FIG. 1 is an exploded, top perspective view of one form of an immunoassay test slide constructed in accordance with the present invention.

Referring initially to FIGS. 9-20 of the drawings, it will be seen that an immunoassay test slide 2 constructed in accordance with the present invention includes a substantially leakproof housing or case 4 formed of two sections—a cover piece 6, and a bottom piece 8 joinable to the cover piece 6. The housing or case 4 defined by the cover piece 6 and the bottom piece 8, when joined together, defines an interior cavity 10 in which is situated an absorbent material 12, also referred to herein as a porous carrier matrix or a fluid flow matrix, as will be described in greater detail.

The cover piece 6 and the bottom piece 8 of the housing 4 are formed from a plastic material, such as polystyrene, polypropylene or polyethylene. Each of the cover piece 6 and the bottom piece 8 includes an inner surface 14, 18, facing the interior cavity 10 of the housing 4, and an opposite outer surface 22, 24 which is exposed. The bottom piece 8 includes one or more projections or ribs 28 extending outwardly from the inner surface 18 of the bottom piece, which ribs 28 are set slightly inwardly from the peripheral edge of the bottom piece 8. The ribs 28 are provided to help secure the cover piece 6 to the bottom piece 8, i.e. ribs 28 provide material that can flow during a welding operation.

The cover piece 6 includes a continuous side wall 30 which extends about the periphery of the cover piece. The preferred thickness of the side wall 30 of the cover piece 6 is preferably equal to the distance the ribs 28 of the bottom piece 8 are set inwardly from the peripheral edge thereof so that, when the cover piece 6 is mounted on the bottom piece 8, the lower edge of the side wall 30 of the cover piece rests on the inner surface 18 of the bottom piece 8, with the outer surface of the side wall 30 being flush with the peripheral edge of the bottom piece 8, and further with the ribs 28 of the bottom piece being situated in contact with or in close proximity to the inner surface of the side wall 30 of the cover piece. Of course, it should be realized that the structure described previously with respect to the cover piece 6 and the bottom piece 8 may be reversed, that is, with the ribs 28 situated on the cover piece 6, and the side wall 30 situated on the bottom piece 8, and such structure is envisioned to be within the scope of the present invention.

The cover piece 6 and the bottom piece 8 are joined together with an adhesive or by heat sealing the two pieces together so as to form a substantially leakproof seal for the housing 4 of the immunoassay test slide. Preferably, portions of the cover piece 6 and bottom piece 8 may be joined together by melting those portions, such as by sonic welding or heat stamping, those portions being allowed to harden and fuse together.

For added strength, and to further facilitate the positioning of the cover piece 6 with respect to the bottom piece 8 when the two pieces are joined together, the cover piece 6 may include one or more (preferably four) posts 32 which extend perpendicularly outwardly from the inner surface 14 of the cover piece 6 a predetermined distance into the interior cavity 10. In addition, the bottom piece 8 may include one or more (preferably four) columns or supports 34 extending perpendicularly outwardly from the inner surface 18 of the bottom piece 8 a predetermined distance into the interior cavity 10. Each column or support 34 of the bottom piece includes a bore 36 formed at least partially axially therein, which is dimensioned to receive a corresponding post 32 of the cover piece 6. The columns or supports 34 of the bottom piece 8 are positioned to be in alignment with the posts 32 of the cover piece 6 so that, when the cover piece 6 is mated to the bottom piece 8, the posts 32 of the cover piece are received by the bores 36 in the supports or columns 34 of the bottom piece, with the free ends of the posts 32 preferably resting on the inner surface 18 of the bottom piece 8 within their respective columns or supports 34. The posts 32 and columns 34 respectively of the cover piece 6 and bottom piece 8 add further strength and rigidity to the immunoassay test slide 2, especially for the interior portion thereof, and help maintain the overall thickness of the housing 4 of the immunoassay test slide 2 to a desired dimension. Of course, it should be realized that the positioning of the posts 32 and columns 34 may be reversed, that is, with the posts 32 extending outwardly from the inner surface 18 of the bottom piece 8, and the columns 34 extending outwardly from the inner surface 14 of the cover piece 6, and such structure is envisioned to be within the scope of the present invention.

The cover piece 6 of the immunoassay test slide 2 has an opening 38 formed through the thickness thereof which may be circular, rectangular, as shown in the drawings, oval in shape. This top opening 38 is provided so that a precise amount of a sample fluid, such as blood, serum and the like, and reagents may be metered onto the test slide 2 and deposited on the absorbent material 12 (the porous carrier matrix or fluid flow matrix) situated under the opening 38, by a sample metering device of the dry chemistry analytical instrument, such as disclosed in the aforementioned Heidt, et al. '229 patent and the Rich, et al. published application, as will be described in greater detail. Furthermore, the bottom piece 8 may have an opening 40 formed through the thickness thereof, which bottom opening 40 is situated in alignment with the top opening 38 of the cover piece 6 when the two pieces are mated together. The bottom opening 40 is provided so that light emitted by a reflectometer or fluorometer of the analytical instrument may pass therethrough and impinge on the fluid flow matrix 12 within the immunoassay test slide 2, and be reflected or fluoresced thereby, the reflected or fluoresced light being detected by the reflectometer or fluorometer during measurements conducted on the immunoassay test slide as it is moved over the reflectometer or fluorometer by a transport mechanism of the analytical instrument. The bottom opening 40, like the top opening 38, may be rectangular, oval or, as shown in the drawings, circular in shape.

Both the top opening 38 in the cover piece 6 and the bottom opening 40 in the bottom piece 8 are situated substantially centrally on each respective piece and in alignment with each other, and are further situated essentially between the four posts 32 and columns 34.

If a bottom opening 40 provided, then a transparent or clear (light transmissive) thin sheet of material 42, such as Mylar, may be placed over the bottom opening and adhesively joined or heat sealed to the inner surface 18 the bottom piece 8 within the interior cavity 10 of the housing, that is, interposed between the inner surface 18 of the bottom piece and the absorbent porous material 12, to insure the leakproofness of the housing 4. Alternatively, the bottom piece 8 may be formed from a transparent or clear (light transmissive) material (glass or plastic, for example), and the bottom opening may be omitted. More specifically, with respect to this alternative embodiment, the material from which the bottom piece 8 is fabricated is chosen to allow visible or infrared light, or more preferably, light at a wavelength of about 645 nanometers, to permeate therethrough. Light emitted by the reflectometer or fluorometer of the analytical instrument will pass through the transparent Mylar cover 42 or the transparent bottom piece 8 to impinge on the absorbent material 12 when the analytical instrument is conducting reflectance or fluorescence measurements on the immunoassay test slide 2.

Figure 12:
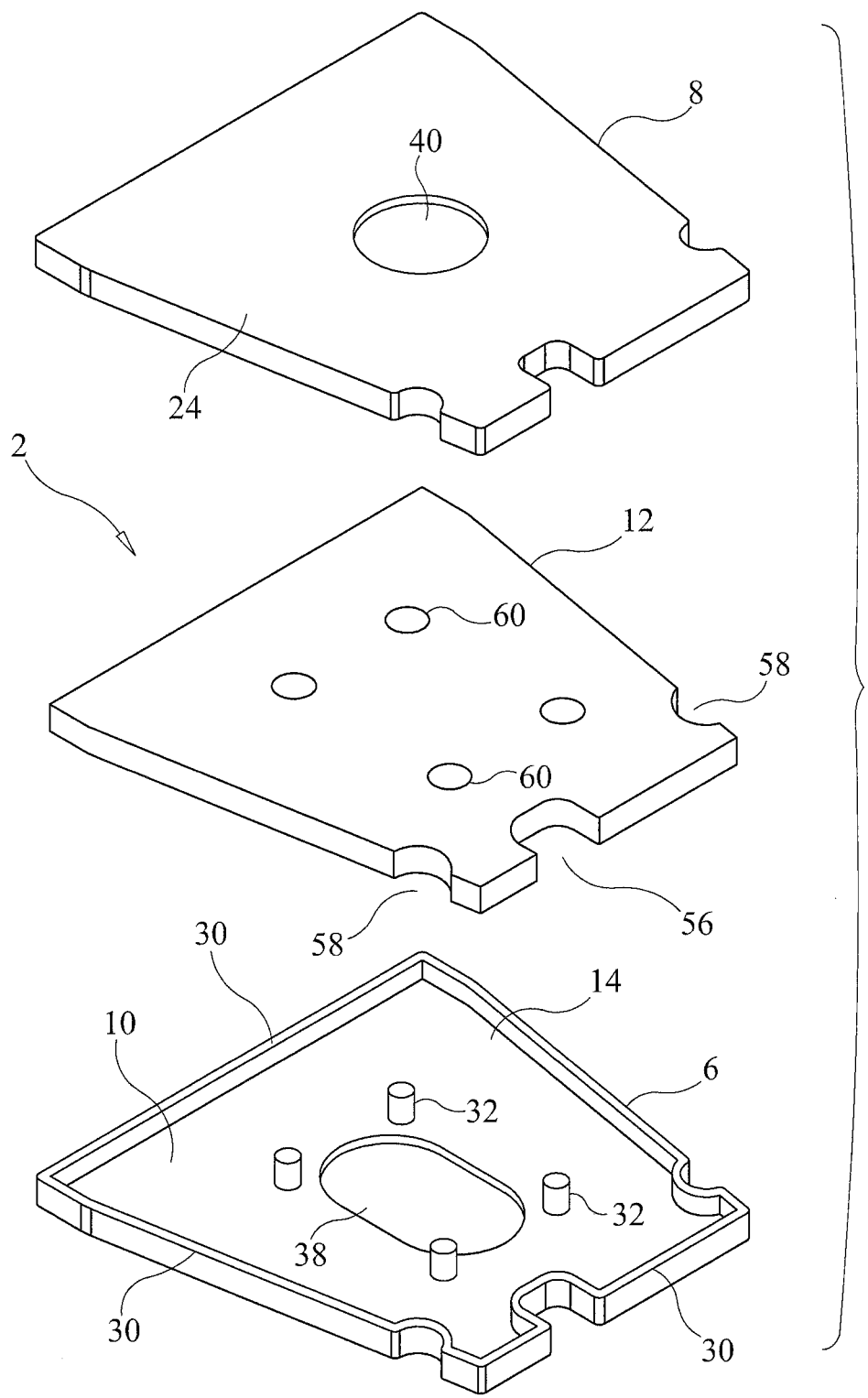
FIG. 12 is an exploded, bottom perspective view of the immunoassay test slide of the present invention shown in FIGS. 9-11.
Figure 12A:
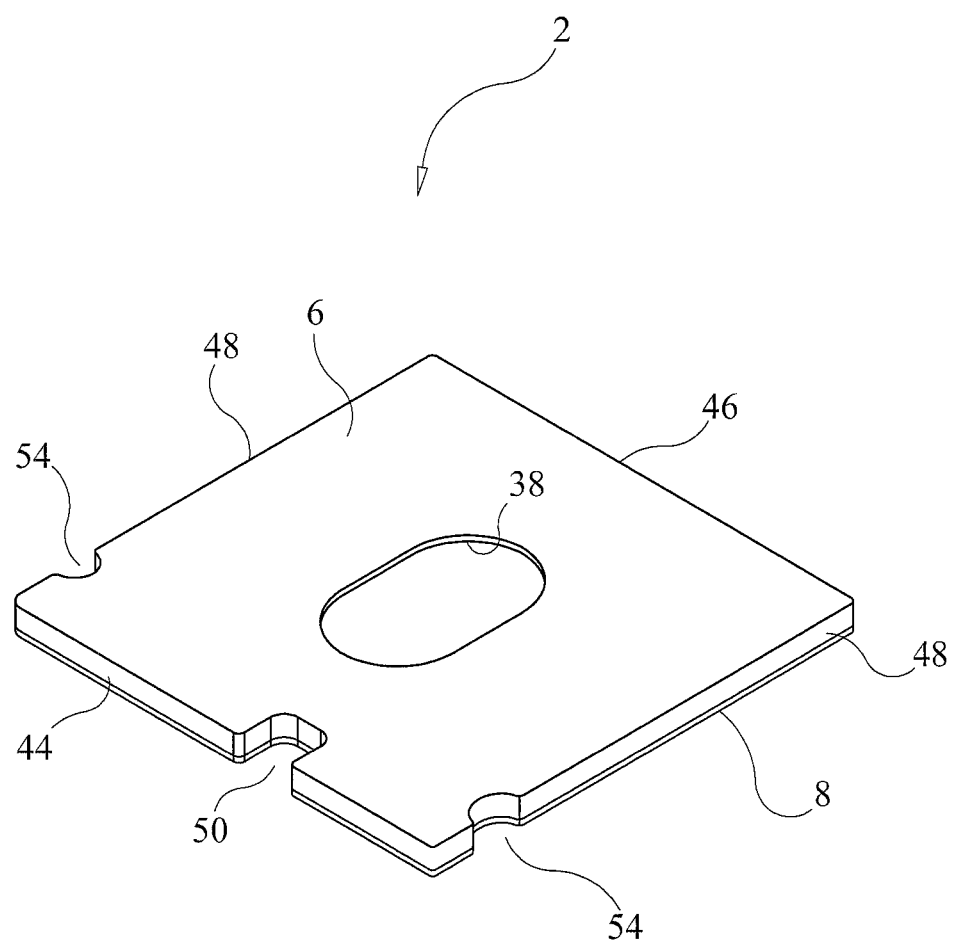
FIG. 12A is a top perspective view of the immunoassay test slide of the present invention having an alternative shape than that shown in FIGS. 9-12.

The housing 4 of the immunoassay test slide defined by the cover piece 6 and the bottom piece 8, when joined together, preferably has an overall rectangular shape like that of the conventional dry chemistry reagent tests slides disclosed in the aforementioned Heidt, et al. '229 patent, or an overall trapezoidal shape like the chemical reagent test slides disclosed in the aforementioned Rich, et al. published application. Thus, the housing 4 includes a front wall 44, a rear wall 46 situated opposite the front wall, and two opposite lateral walls 48, each of which is defined at least in part by the side wall 30 of the cover piece 6. If the immunoassay test slide housing 4 takes on a rectangular shape, then each wall 44-48 is perpendicularly joined to its next adjacent wall, as shown in FIG. 12A. If the immunoassay test slide housing has a trapezoidal shape, such as shown in FIGS. 9-12 and 12A-20, then the front and rear walls 44, 46 are generally parallel to each other and the rear wall 46 has a length which is greater than that of the front wall 44, and the opposite lateral walls 48 are non-parallel to each other and mutually converge from the rear wall 46 toward the front wall 44.

Furthermore, the overall dimensions of the immunoassay test slide 2, and the overall thickness thereof, are substantially the same as the dimensions and thickness of the dry chemistry reagent tests slides disclosed in the Heidt, et al. patent and the Rich, et al. published application. In this way, the immunoassay test slides 2 may be used with such analytical instruments disclosed in the Heidt, et al. patent and the Rich, et al. published application, and with other conventional analytical instruments, just like the dry chemistry test slides having a frame surrounding a film portion carrying a reagent, as disclosed in the aforementioned Heidt, et al. patent and the Rich, et al. published application.

In addition, each of the cover piece 6 and the bottom piece 8 is formed to include, and to define the housing 4 of the immunoassay test slide 2 with, an indexing notch 50 for proper orientation of the test slide on the analytical instrument, and lateral side recesses 54 used for loading the test slides on the analytical instrument, in the same manner and in the same locations as the notch and lateral side recesses included in the dry chemistry test slides disclosed in the aforementioned Heidt, et al. patent and the Rich, et al. published application. It should be noted that the side wall 30 of the cover piece 6 extends about the notch 50 and the lateral side recesses 54 to insure that the housing 4 is substantially leakproof.

As mentioned previously, an absorbent material 12 (i.e., the porous carrier matrix or fluid flow matrix) is disposed within the confines of the housing cavity 10. The fluid flow matrix 12 is preferably die cut from a sheet of such material and shaped to conform to the inner dimensions of the housing 4. More specifically, and as can be seen in the drawings, the fluid flow matrix 12 includes a notched-out portion 56 and recessed side portions 58 to accommodate the notch 50 and lateral recesses 54 formed in the housing 4, and includes four cutouts 60 formed through its thickness which are aligned with and dimensioned to receive the columns or supports 34 of the bottom piece 8 so as not to interfere with the ability of the posts 32 of the cover piece 6 being received by the bores 36 of the columns of the bottom piece 8. Thus, the columns 34 and posts 32 respectively of the bottom piece 8 and cover piece 6, passing through the thickness of the fluid flow matrix 12, help to hold the fluid flow matrix in place within the interior cavity 10 of the housing, without shifting.

As further mentioned previously, the fluid flow matrix 12 is dimensioned and shaped to fit within the confines of the interior cavity 10 of the test slide housing 4. Preferably, however, the matrix is dimensioned to be slightly smaller than the dimensions of the interior cavity 10 so that its lateral edges are spaced slightly away from the inner surface of the side wall 30 of the cover piece 6 to define a channel or well 62 (see FIG. 20) between the matrix 12 and side wall 30 at least partially about the periphery of the housing. This channel or well 62 is provided to receive any overflow of fluid sample, reagent or wash solution from the matrix 12 which is envisioned to become saturated with such fluids. The well or channel 62 provides capacity in excess of the volume of the fluid sample, reagents and wash solutions saturating the fluid flow matrix 12. The preferred volume of the interior cavity 10 defined by the housing 4 of the immunoassay test slide is between about 20 microliters and about 200 microliters, and is preferably about 270 microliters. In various alternative embodiments of the immunoassay test slide 2 of the present invention, the absorbent matrix 12 may have a volume that occupies about 50 percent, or about 60 percent, or about 70 percent, or about 80 percent, or about 90 percent, of the interior space 10 defined by the housing.

The flow matrix material preferably possesses the following characteristics: (1) low non-specific affinity for sample materials and labeled specific binding reagents, (2) ability to transport a liquid by capillary action over a distance with a consistent liquid flow across the matrix 12, and (3) ready binding to immobilized specific binding reagents (e.g., by covalent or non-covalent attachment or by physical entrapment). Materials possessing these characteristics include fibrous mats composed of synthetic or natural fibers (e.g., glass or cellulose-based materials or thermoplastic polymers, such as, polyethylene, polypropylene, or polyester); sintered structures composed of particulate materials (e.g., glass or various thermoplastic polymers); or cast membrane films composed of nitrocellulose, nylon, polysulfone or the like (generally synthetic in nature). The invention may utilize a flow matrix 12 composed of sintered, fine particles of polyethylene, commonly known as porous polyethylene, such as sintered polyethylene beads; preferably, such materials possess a density of between 0.35 and 0.55 grams per cubic centimeter, a pore size of between 5 and 40 microns, and a void volume of between 40 and 60 percent. Particulate polyethylene composed of cross-linked or ultra high molecular weight polyethylene is preferable. A flow matrix 12 composed of porous polyethylene possesses all of the desirable features listed above, and in addition, is easily fabricated into various sizes and shapes. A particularly preferred material is 10-15 micron porous polyethylene from Chromex Corporation FN#38-244-1 (Brooklyn, N.Y.). Another preferred material is Fusion 5™ lateral flow matrix available from Whatman, Inc., USA.

The porous carrier matrix 12 may be made from a material which has a low affinity for the analyte and test reagents. This is to minimize or avoid pretreatment of the test matrix to prevent nonspecific binding of analyte and/or reagents. However, materials that require pretreatment may provide advantages over materials that do no require pretreatment. Therefore, materials need not be avoided simply because they require pretreatment. Hydrophilic matrices generally decrease the amount of non-specific binding to the matrix 12.

In one aspect, the porous carrier matrix 12 may have an open pore structure with an average pore diameter of 1 to 250 micrometers and, in further aspects, about 3 to 100 micrometers, or about 10 to about 50 micrometers. The matrices 12 are from a few mils (0.001 in) to several mils in thickness, typically in the range of from about 10 mils to about 20 mils and, most preferably, about 16 mils.

An example of a suitable porous carrier matrix 12 in which omni-directional flow occurs is the high density or ultra high molecular weight polyethylene sheet material manufactured by Porex Technologies Corp. of Fairburn, Ga., USA. This material is made from fusing spherical particles of ultra-high molecular weight polyethylene (UHWM-PE) by sintering. This creates a porous structure with an average pore size of eight to 20 microns, depending on the size of the particles (20 to 60 microns, respectively). The polyethylene surface is treated with an oxygen plasma and then coated with alternating layers of polyethylenimine (PEI) and poly acylic acid (PAA) to create surfactant-free hydrophilic surface having a wicking rate of 0.01-0.5 cm/s.

While matrices 12 made of polyethylene have been found to be highly satisfactory, omni-directional flow materials formed of other olefin or other thermoplastic materials, e.g., polyvinyl chloride, polyvinyl acetate, copolymers of vinyl acetate and vinyl chloride, polyamide, polycarbonate, polystyrene, etc., can be used. Examples of suitable materials include Magna Nylon Supported Membrane from GE Osmonics (Minnetonka, Minn.), Novylon Nylon Membrane from CUNO Inc. (Meriden, Conn.) and Durapore Membrane from Millipore (Billerica, Mass.).

The matrix materials may be slit, cut, die-cut or punched into a variety of shapes prior to incorporation into the immunoassay test slide 2 of the present invention.

Other porous materials suitable for the absorbent carrier 12 may include natural, synthetic, or naturally occurring or synthetically modified materials: papers (fibrous) or membranes (microporous) of cellulose materials such as paper, cellulose, and cellulose derivatives such as cellulose acetate and nitrocellulose, fiberglass, glass fiber, cloth, both naturally occurring (e.g., cotton) and synthetic (e.g., nylon); porous gels such as silica gel, agarose, dextran, and gelatin; porous fibrous matrices; starch based materials, cross-linked dextran chains; ceramic materials; olefin or thermoplastic materials including films of polyvinyl chloride, polyethylene, polyvinyl acetate, polyamide, polycarbonate, polystyrene, copolymers of vinyl acetate and vinyl chloride and combinations of polyvinyl chloride-silica; and the like. This list is representative, and not meant to be limiting.

The porous materials, and specifications, for the fluid flow matrix set forth in U.S. Pat. No. 5,726,010, for example, mentioned previously may be used in the immunoassay test slide 2 of the present invention, and such disclosures are incorporated herein by reference.

One or more analyte capture reagents are immobilized on the fluid flow matrix 12 and situated thereon above the bottom opening 40 formed in the bottom piece 8 and beneath the top opening 38 formed in the cover piece 6. The analyte capture reagent is a molecule which is bound to the matrix and which has a specific affinity for an analyte of interest. Preferably, the affinity arises by virtue of the reagent possessing a complementary three-dimensional structure to the analyte, e.g., as seen in the relationship between an enzyme and a substrate or an antigen and an antibody. Within a given pair, either member may be considered to be the analyte or the capture reagent. This definition serves only to differentiate the component to be detected in the sample (i.e., the analyte) from the reagent included in the immunoassay test slide 2 (i.e., the analyte capture reagent).

As stated above, different analyte capture reagents may be immobilized on the matrix 12 for different tests. For example, one analyte capture reagent may include an immobilized antibody specific for feline immunodeficiency virus, and another may include an immobilized antibody specific feline leukemia virus. A single biological sample (e.g., a sample of feline serum) may be deposited on the slide 2 and assayed for the presence of one or both viruses. The immobilized analyte binding partner may be pre-deposited on the immunoassay test slide 2 prior to its assembly, or may be deposited on the assembled slide and optionally heat dried.

EXAMPLE

T4 Immunoassay

A method of performing an assay using the immunoassay test slide 2 of the present invention will now be described, and reference should be had to FIGS. 21A-28 of the drawings. In the example shown in FIGS. 21A and 21B, an assay is performed of thyroxine (T4) using an antibody-horseradish peroxidase conjugate. For this description, reference should further be had to the aforementioned Rich, et al. published application and the description of the structure and operation of the chemical analyzer therein, but also to FIG. 22, which illustrates a chemical analyzer 64 similar to that disclosed in the Rich, et al. published application, and related FIGS. 23-28 showing referenced components of the chemical analyzer. The assay consumables are envisioned to include the T4 slide; a "CTdx" diluent drawer package which includes a conjugate, a wash buffer and a substrate; and a sample, such as serum or plasma.

The first step in the method is to load all of the consumables into the chemical analyzer. More specifically, one or more of the immunoassay test slides 2 of the present invention are loaded onto a slide inserter mechanism 20 (see FIG. 23) (also reference no. 20 in the Rich, et al. application) situated behind doors 16 (see FIG. 23) of the chemical analyzer (also reference no. 16 in the Rich, et al. application), which open to gain access to one of two slide inserter mechanisms. The slide inserter mechanism loads the immunoassay test slide, among other chemical reagent test slides, onto a slide transport mechanism 26 (see FIG. 24) (also reference no. 26 in the Rich, et al. application). The slide transport mechanism 26 selectively positions the immunoassay test slide under a fluid sample metering device 84 (see FIG. 24) (also reference no. 84 in the Rich, et al. application) and above either or both of a reflectometer 684 (see FIG. 25) (also reference no. 684 in the Rich, et al. application) and a fluorometer 654 (see FIG. 26) (also reference no. 654 in the Rich, et al. application) to conduct colorimetric or fluorescence measurements.

A predetermined volume of fluid sample, such as blood, serum or the like, is added to a sample vial 242 (see FIG. 27) (also reference no. 242 in the Rich, et al. application), and the sample vial is placed on the slide inserter mechanism 20 in a well 206 (see FIG. 27) (also reference no. 206 in the Rich, et al. application) for holding the vial. Furthermore, separate vials containing a liquid conjugate reagent, a wash reagent and a detector reagent (TMB) can be loaded into respective wells formed in a diluent drawer 136 (see FIG. 28) behind door 132 (see reference nos. 36 and 32 in the Rich, et al. application) of the chemical analyzer or in any other suitable location so long as the reagents are accessible to the analyzer's fluid metering system (see Step 1 in FIG. 21A).

Then, in Step 2 (see FIG. 21A), the fluid sample and the conjugate reagent are mixed by the metering device 84 of the chemical analyzer 64 either in a conjugate vial or in a separate empty vial situated in the diluent drawer 136 behind door 132. The mixing of the sample and conjugate may be performed in the manner disclosed in the Rich, et al. published application. The sample/conjugate mixture is then incubated within the chemical analyzer 64 at a predetermined temperature (for example, 37° C.) for a predetermined period of time (for example, five minutes). When the sample and conjugate reagent are mixed, the T4 disassociates from the serum binding, proteins in the fluid sample and then binds to the T4-antibody*HRP.

Figure 21A:
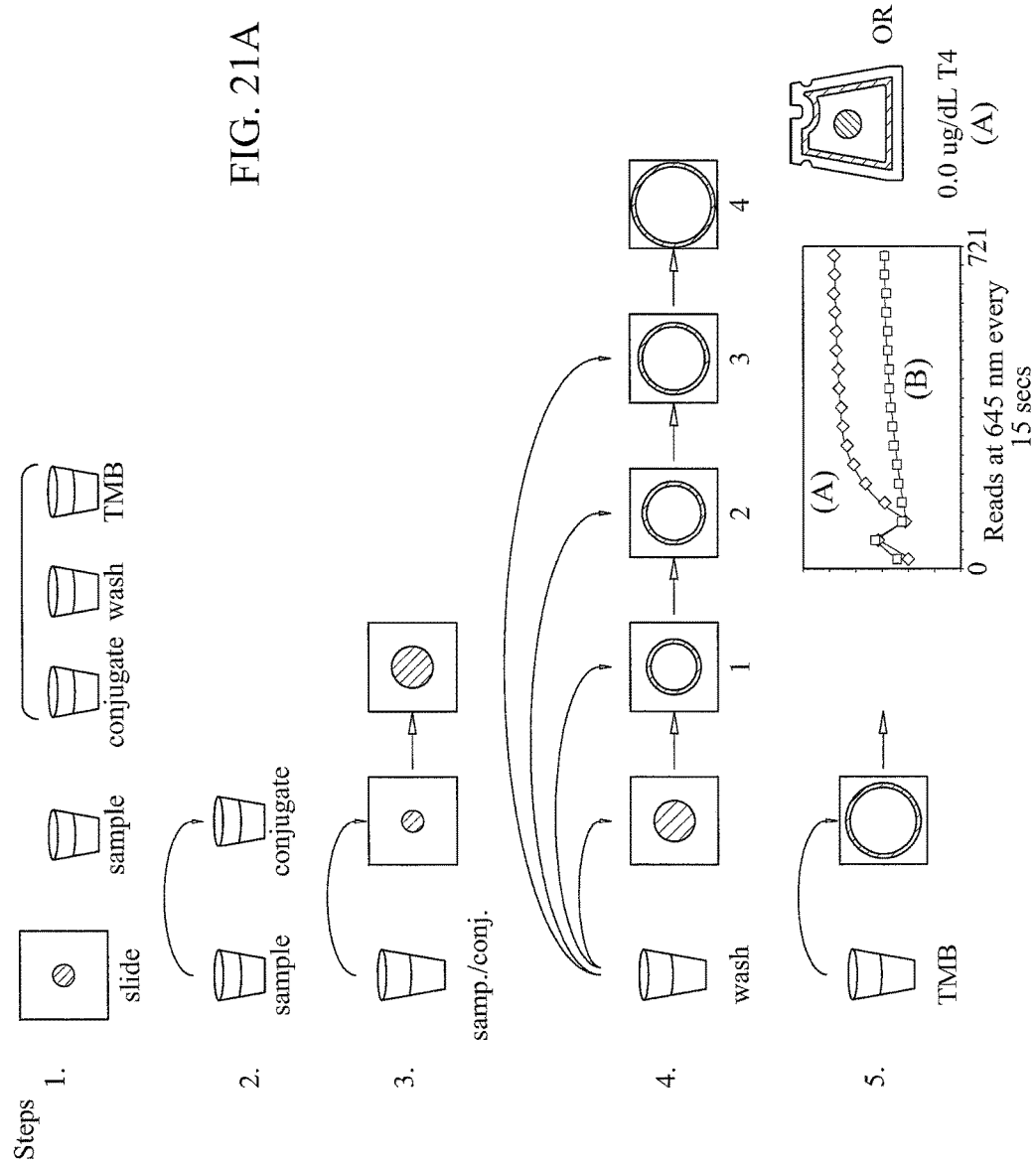
FIG. 21A is diagrammatic illustration of a method of using the immunoassay test slide of the present invention to detect an analyte in a sample fluid.

After incubation, a relatively small amount (preferably 8 microliters) of the sample/conjugate mixture is dispensed on the immunoassay test slide 2 by the metering device 84 of the chemical analyzer, as set forth in Step 3 shown in FIG. 21A. Here, unbound T4-antibody*HRP binds to the immobilized capture reagent spot on the fluid flow matrix 12, which in the example shown is T3-PAA. One useable method of aspirating the sample/conjugate mixture from the vial and depositing the mixture on the immunoassay test slide 2 by the metering device 84 of the chemical analyzer is disclosed in the aforementioned Rich, et al. published application.

Now, in Step 4 shown in FIG. 21A, the immunoassay test slide 2 is washed multiple times. More specifically, the test slide preferably undergoes four washes using 8 microliters of wash reagent for each wash dispensed by the metering device 84 of the chemical analyzer, each wash being preferably spaced apart in time by about 30 seconds. The metering device 84 of the chemical analyzer aspirates preferably at least 32 microliters of wash reagent from a vial in the diluent drawer containing such solution, and periodically dispenses preferably 8 microliters of the wash reagent onto the slide 2. With such washes, the T4-antibody*HRP bound to serum T4 is washed away.

The wash solution is a liquid reagent that serves to remove unbound material from at least the central portion of the fluid flow matrix 12 situated above the bottom opening 40 in the bottom piece 8 or in the region of the matrix 12 which is subjected to measurement tests by the reflectometer or fluorometer. The wash reagent contains a surface active agent, such as a surfactant, or any other component capable of allowing the wash to wet the fluid flow matrix 12. Some other examples of wash reagents are alcohol (e.g. methanol) or any other water miscible organic solvent. Thus, in the example shown in FIGS. 21A and 21B, unbound sample and unbound antibody-horseradish peroxidase conjugate are displaced by the wash reagent. There should be sufficient time allotted between dispensing the sample/conjugate mixture on the slide (Step 3 in FIG. 21A) and the start of the multiple wash step (Step 4 in FIG. 21A) to maximize the binding of the sample analyte to the specific binding reagent.

After waiting about 30 seconds after the fluid flow matrix 12 is washed the fourth time, the substrate, or detector reagent, is dispensed on the immunoassay test slide 2 in a predetermined volume, preferably about 8 microliters (see Step 5 in FIG. 21A). The substrate, or detector reagent, produces a detectable signal upon reaction with the enzyme-antibody conjugate at the central portion of the matrix 12. An example of a detector reagent, or substrate, which produces an insoluble end product following reaction with the enzyme, horseradish peroxidase, is tetramethylbenzidine, or TMB, such as TMBlue, available from TSI Incorporated of Worcester, Mass., Part no. TM 101. The end product produced by the TMBlue substrate is a dye that absorbs light. In the example shown in FIGS. 21A and 21B, the T4-antibody*HRP bound to the spotted T3-PAA develops color, which is detectable by the reflectometer 684 of the chemical analyzer. Alternatively, a detector reagent, or substrate, may be chosen to cause light to be emitted from the slide upon eradiation, e.g. fluorescence, by a fluorometer 654 of the chemical analyzer. The degree of color change of the matrix is reflective of the amount of analyte in the fluid sample. Examples and descriptions of various conjugate reagents, specific binding reagents, fluid flow matrices, wash reagents and detector reagents and substrates are disclosed in the aforementioned U.S. Pat. No. 5,726,010 and the patents and publications cited therein, and such disclosures are incorporated herein by reference.

Figure 21B:
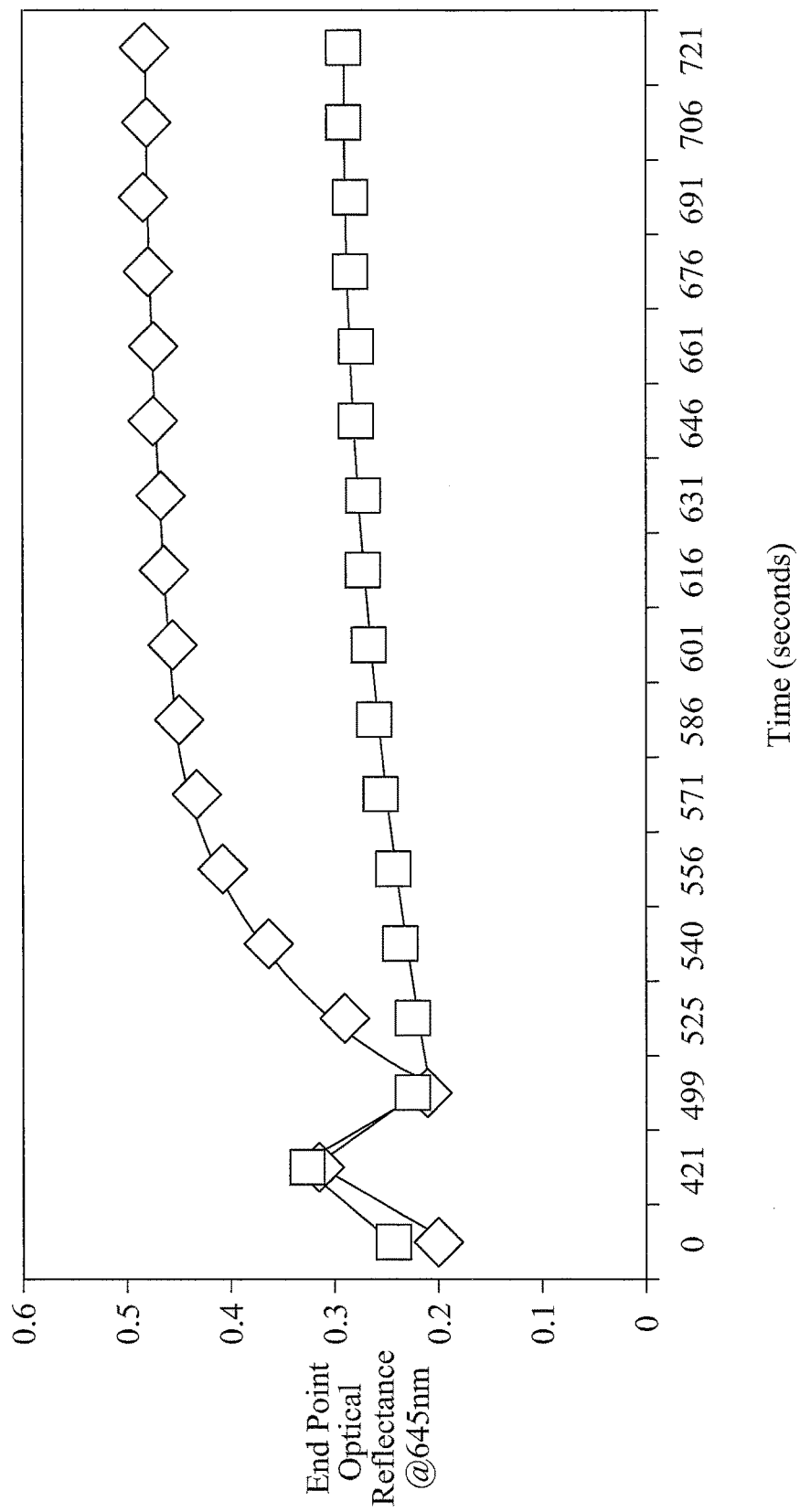
FIG. 21B is a graph of reflectance measurements versus time illustrating exemplary results of tests performed on a T4 slide in accordance with the method of the present invention shown in FIG. 21A.
Figure 22:
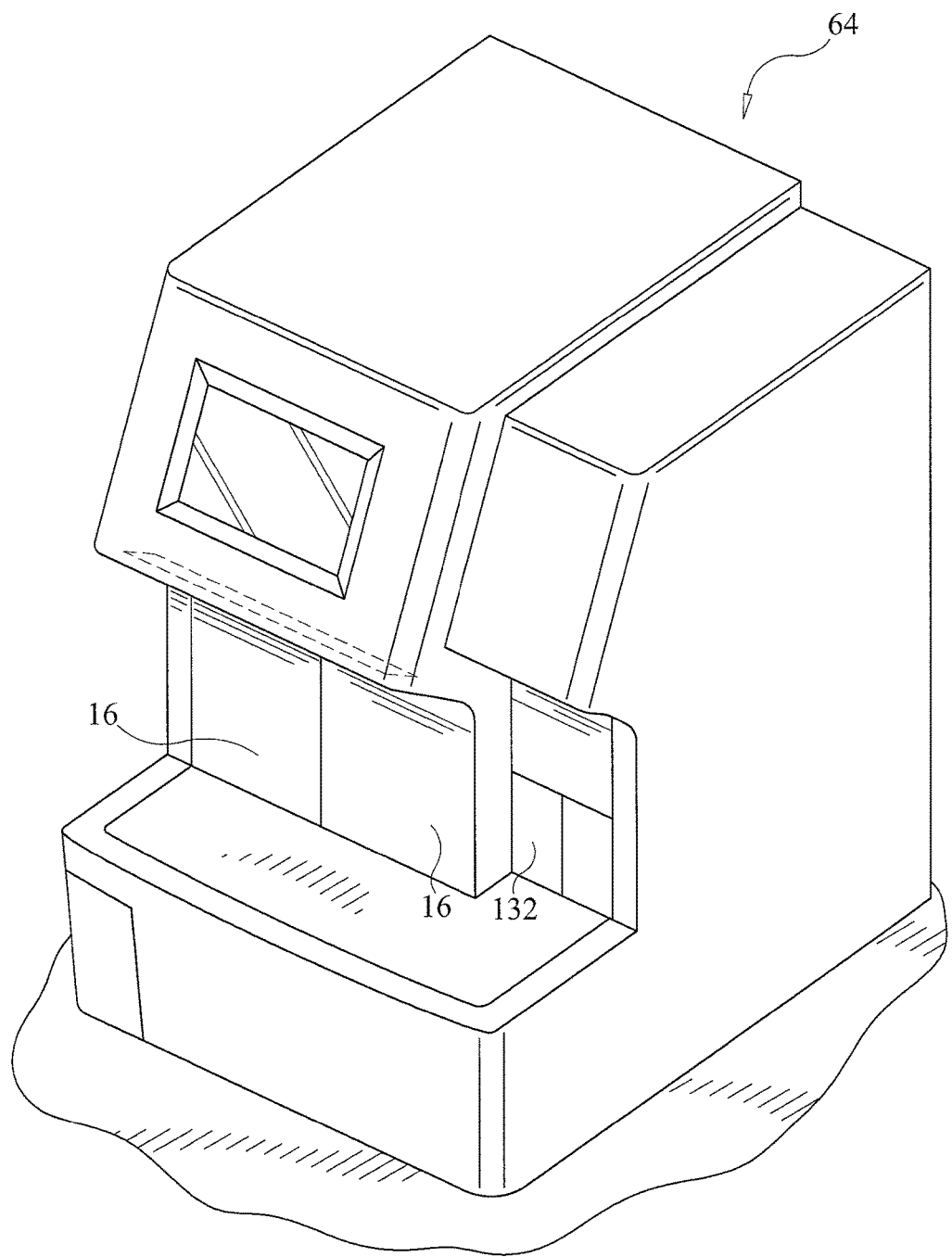
FIG. 22 is a front isometric view of a chemical analyzer formed in accordance with one form of the present invention for use with both conventional dry chemistry analytical slides and the immunoassay test slide of the present invention.
Figure 23:
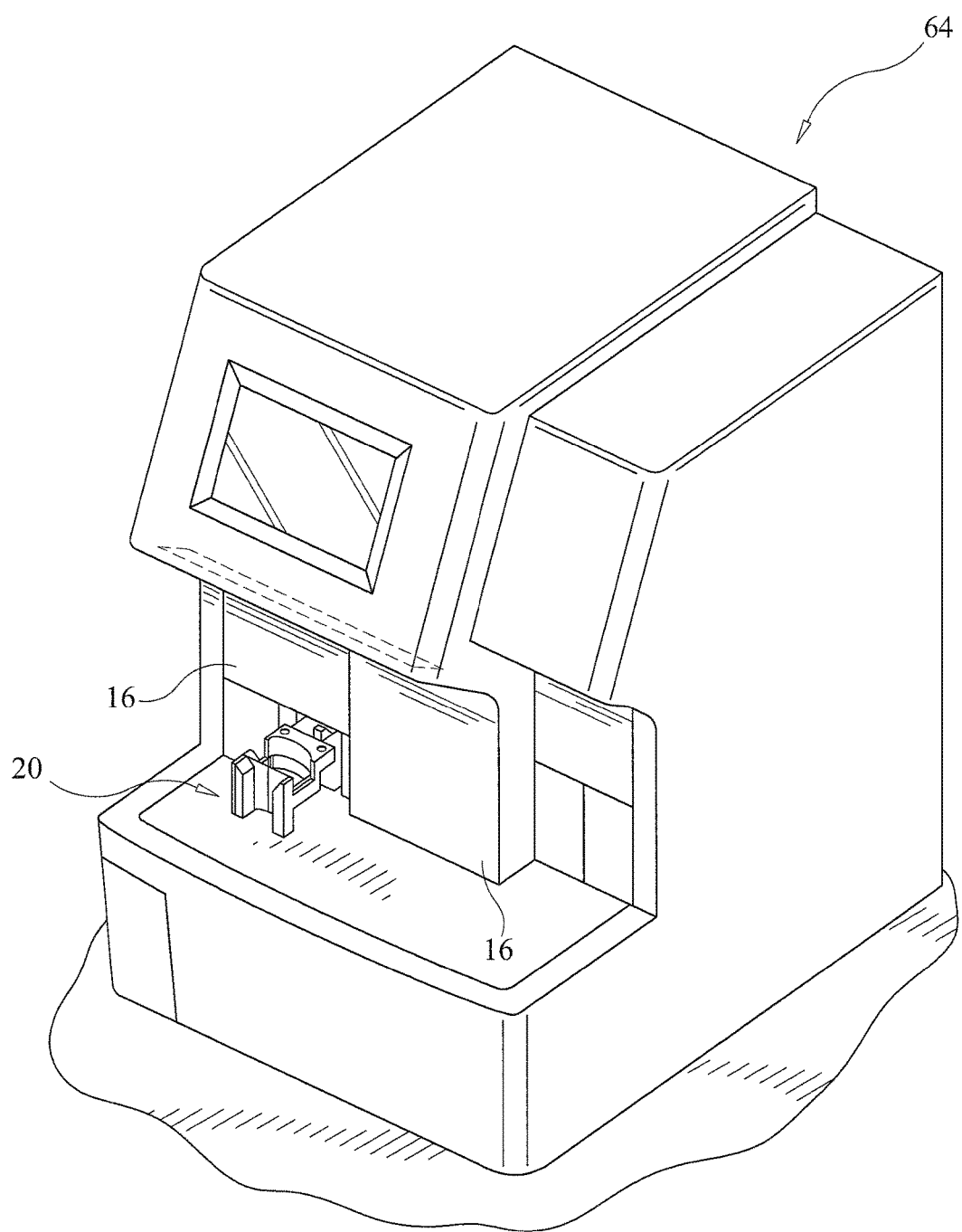
FIG. 23 is a front isometric view of the chemical analyzer shown in FIG. 22, illustrating a first sliding door on the front face of the analyzer being open and a first slide inserter mechanism of the chemical analyzer extending beyond the front face of the analyzer housing.
Figure 24:
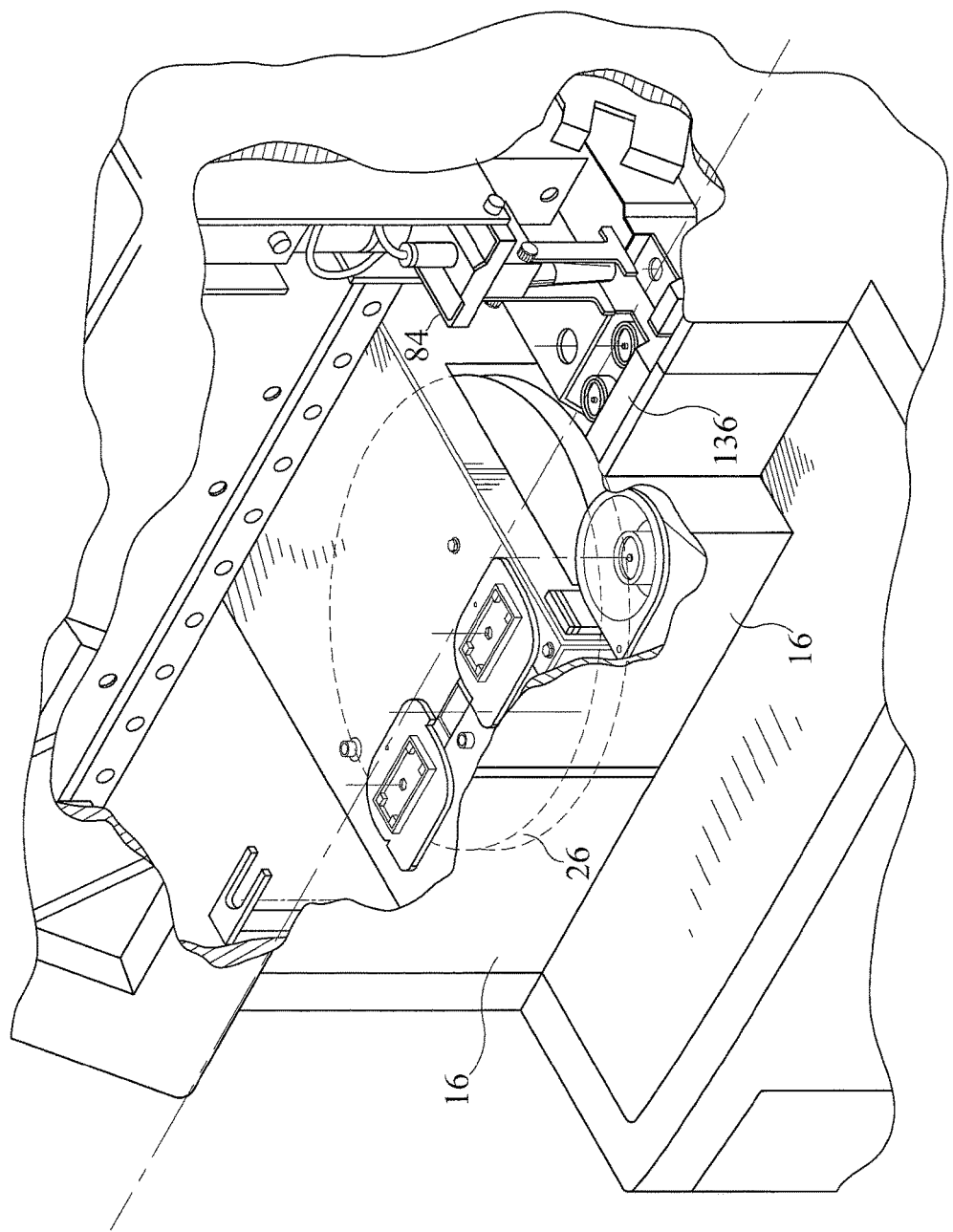
FIG. 24 is a front isometric view of the chemical analyzer, with the housing thereof partially broken away, and illustrating various components of the analyzer of the present invention.
Figure 25:
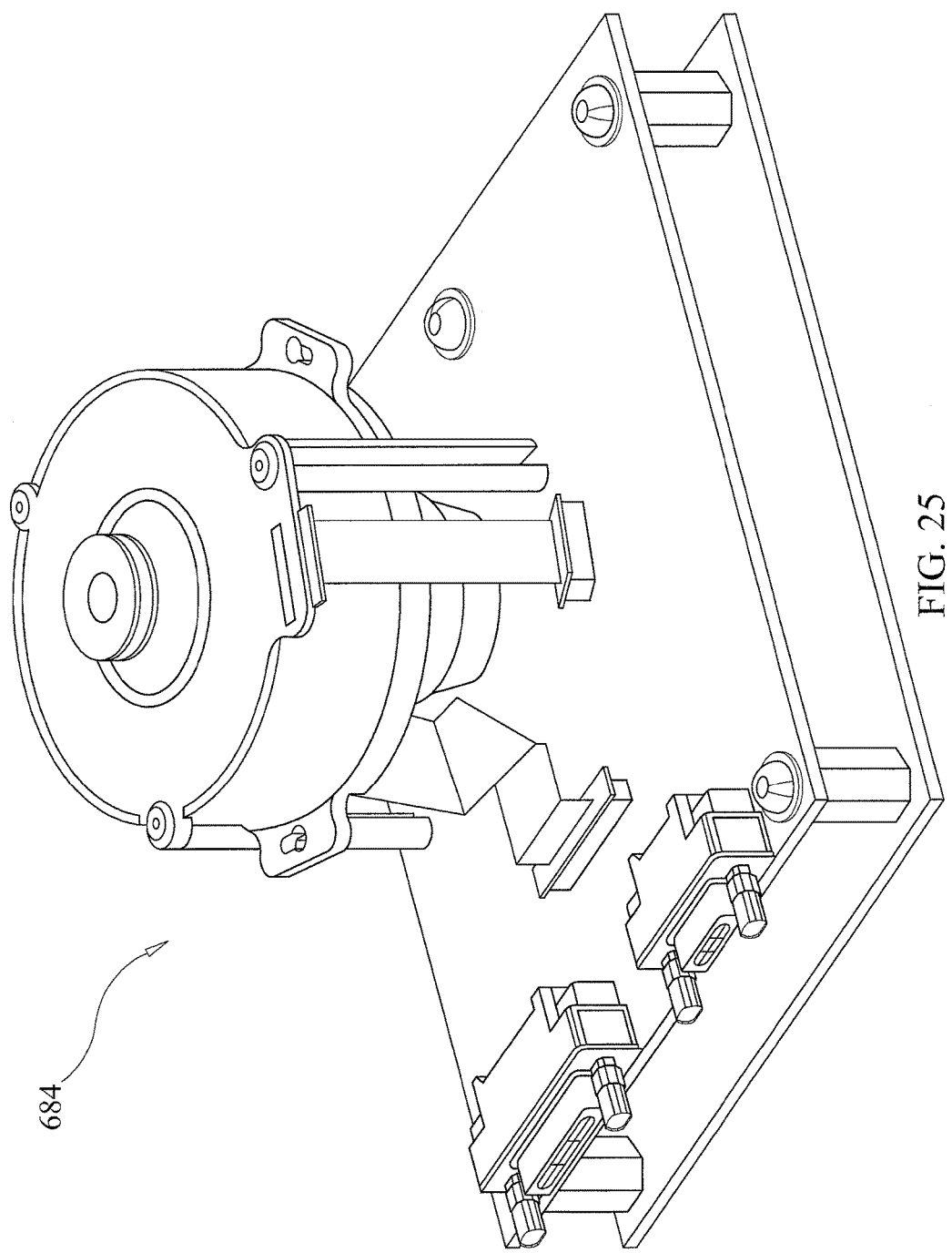
FIG. 25 is a top isometric view of a reflectometer used in the chemical analyzer of the present invention, with portions of the reflectometer partially broken away.
Figure 26:
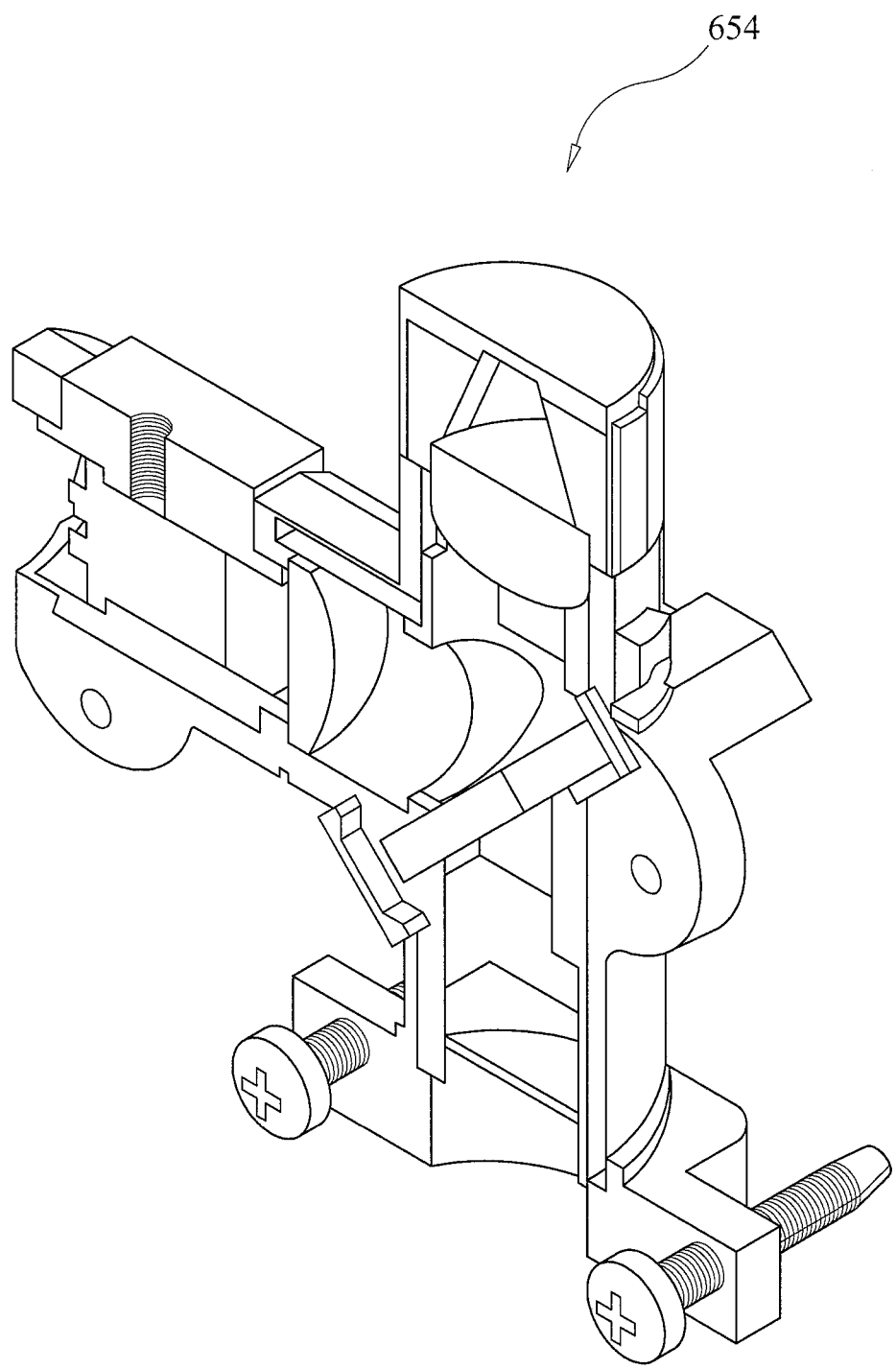
FIG. 26 is a cut-away pictorial illustration of a fluorometer used in the chemical analyzer of the present invention.
Figure 27:
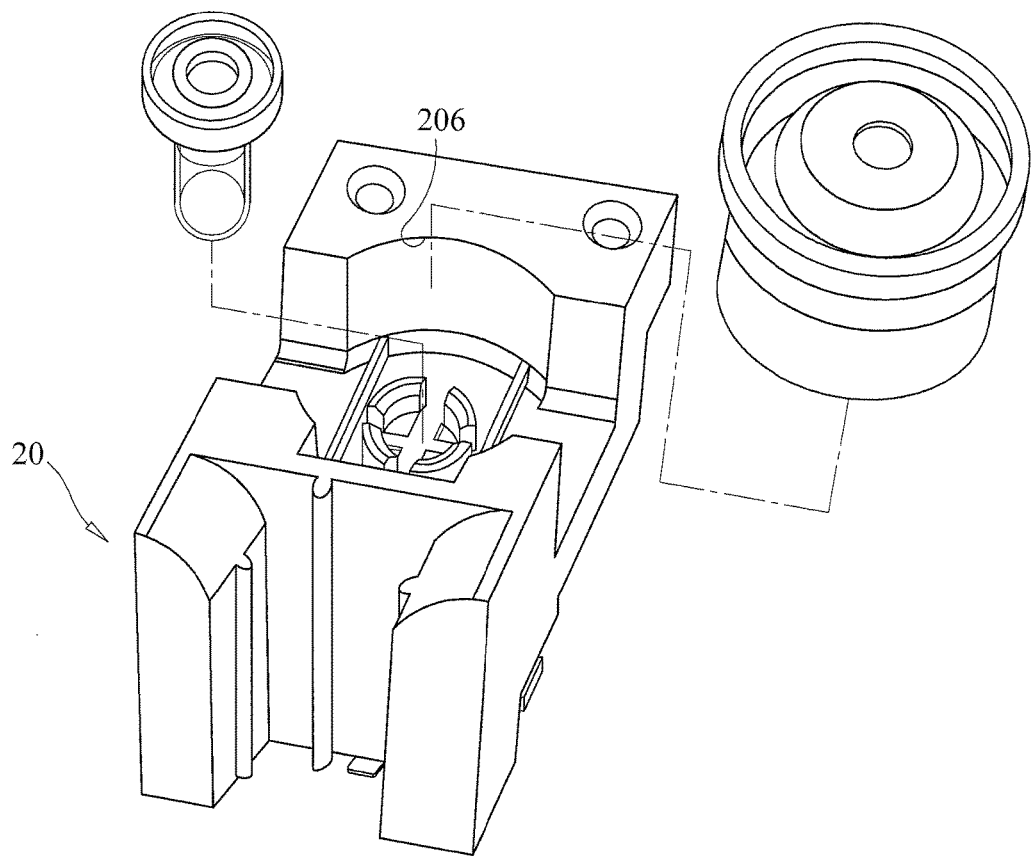
FIG. 27 is a front isometric view of a portion of the slide inserter mechanism used in the chemical analyzer of the present invention, and illustrating the placement of either a centrifuge rotor or a sample vial thereon.
Figure 28:
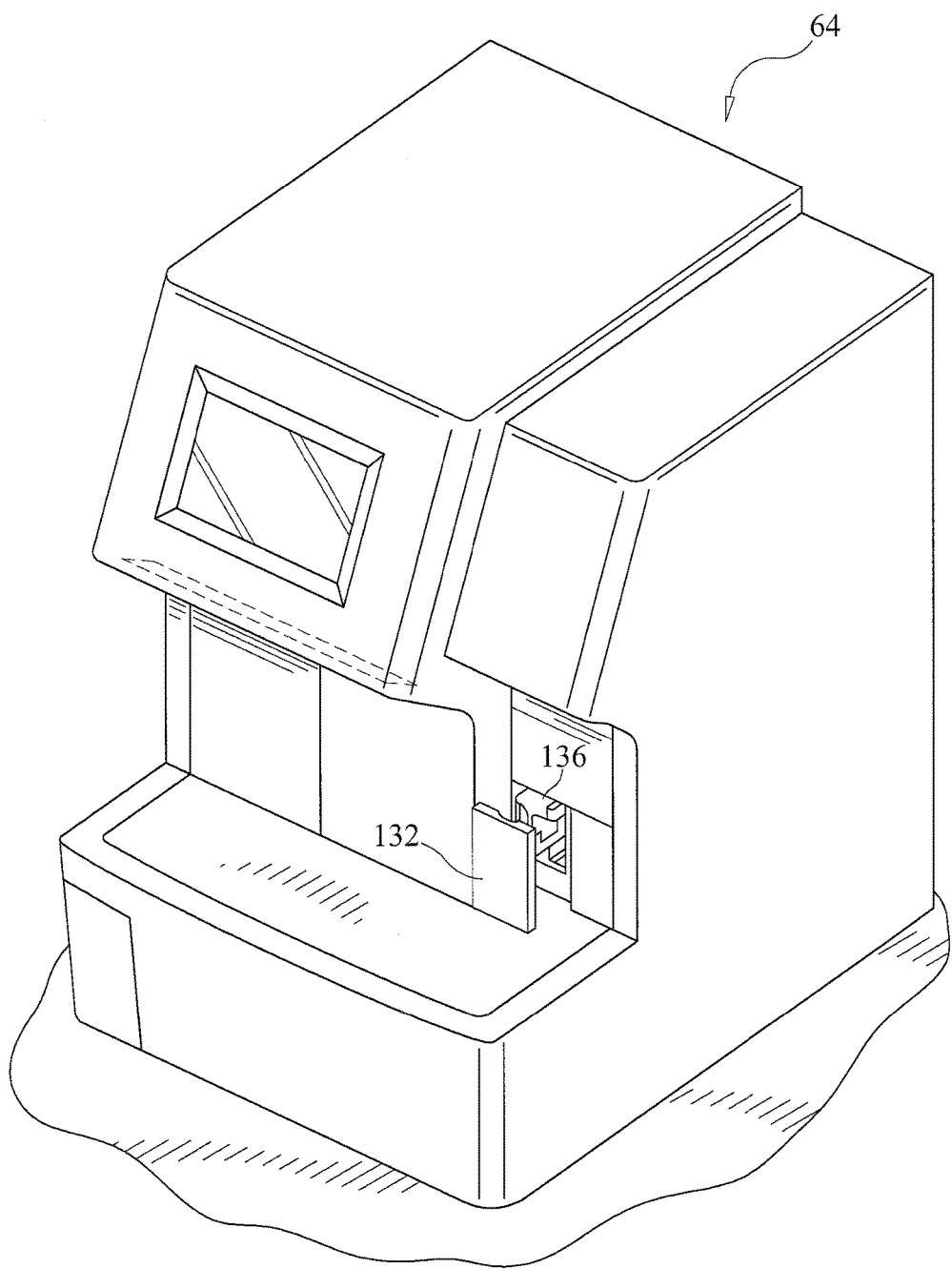

FIG. 21B shows a graph plotting exemplary test results of reflectance measurements versus time for a T4 slide following the steps of the method described above and shown in FIG. 21A. Reflectance measurements are preferably performed at 645 nanometers every 15 seconds on the T4 slide spotted with sample (labeled as "7.0 ug/dL T4" in FIG. 21A) and preferably a control T4 slide not spotted with sample (labeled as "0.0 ug/dL T4" in FIG. 21A). Exemplary reflectance measurements of both the sample T4 slide (shown by the line with diamonds) and the control T4 slide (shown by the line with squares) are plotted in the graph of FIG. 21B.

EXAMPLE

Feline Pancreatic Lipase (fPL) Immunoassay

The manufacture and use of a Feline Pancreatic Lipase (fPL) immunoassay test slide formed in accordance with the present invention will now be described. The fPL immunoassay test slide may have the structure shown in the embodiment of FIGS. 9-20 or the embodiments shown in FIGS. 1-4, as will be described in greater detail.

Preferably, in forming the fPL immunoassay test slide, the porous matrix 12, which is preferably formed from a Fusion 5™ absorbent material, is placed into the slide housing 4 having a crystal clear (i.e., light transmissive) bottom side. Ten microliters of fPL 17A reagent particles are spotted onto the porous matrix (either on the top side or the bottom side of the matrix). The spotted slides are then dried in a drying tunnel for about 0.5 hour at about 95° Fahrenheit. The dried slides may then be used immediately or stored at preferably about 4° Celsius.

Figure 5:
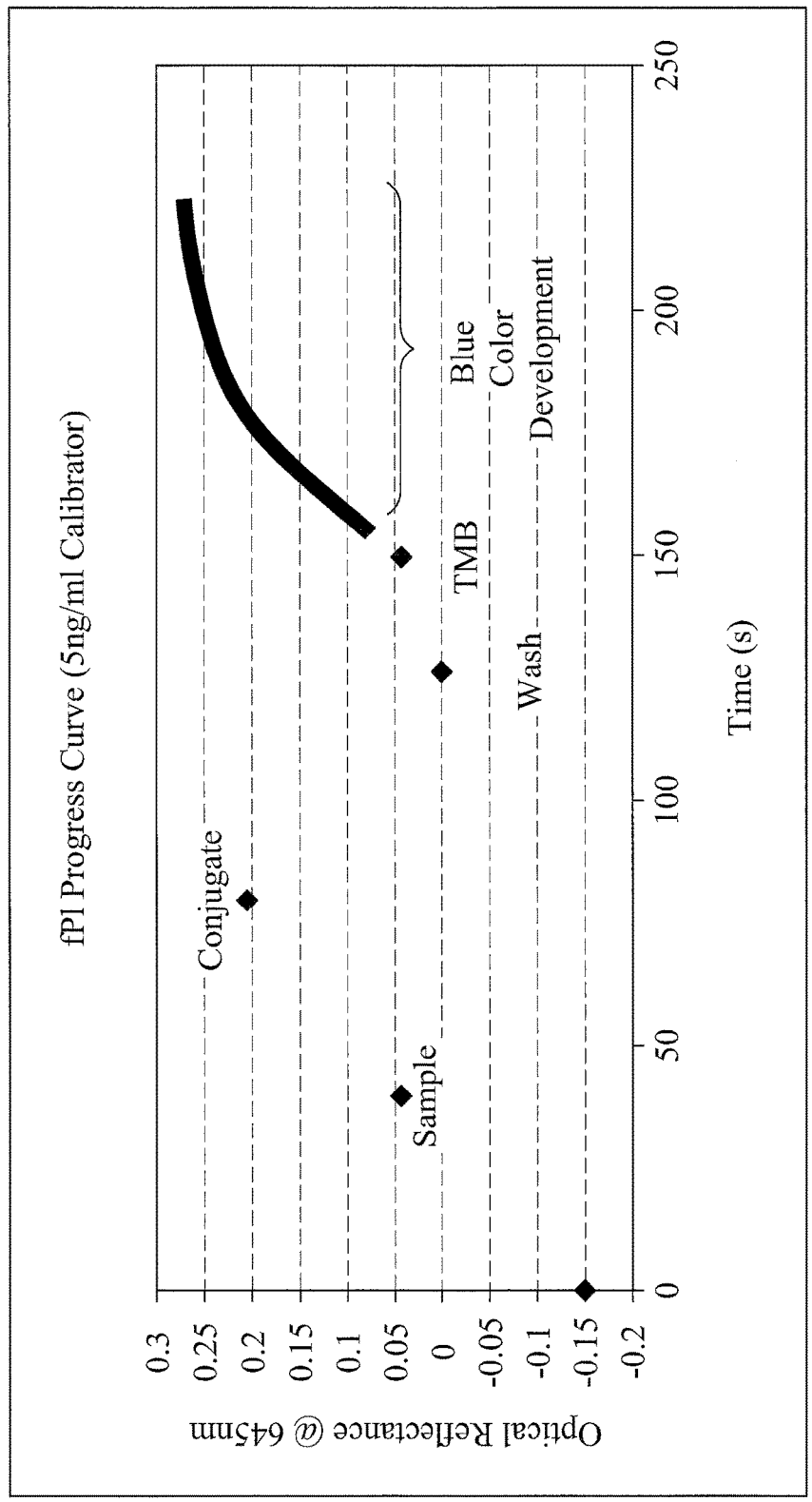
FIG. 5 is a graph of optical reflectance versus time showing the progress curve for a two-step test protocol using an fPL immunoassay test slide formed in accordance with the present invention.
Figure 6:
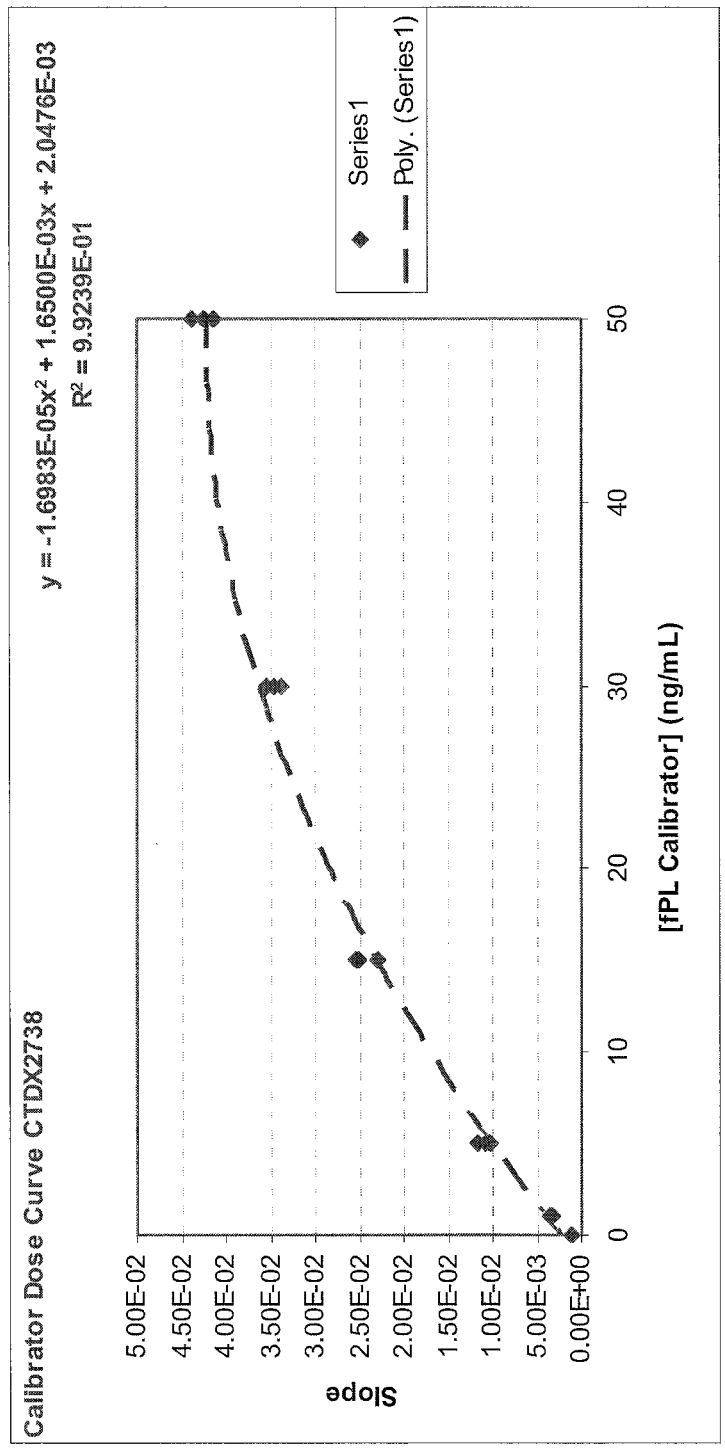
FIG. 6 is a graph of optical reflectance versus nanograms/milliliters showing the calibrator dose curve for a two-step test protocol using an fPL immunoassay test slide formed in accordance with the present invention.

A two-step protocol for testing for Feline Pancreatic Lipase is described below and shown in FIGS. 5 and 6 of the drawings. Sixteen microliters of sample are aspirated from a sample cup, and then dispensed onto the test slide at 4 microliter aliquot portions. Then, 16 microliters of conjugate are aspirated from the conjugate cup, and then dispensed onto the slide at 4 microliter aliquot portions. After this, 24 microliters of a wash buffer are aspirated from the wash cup, and then dispensed onto the slide at 4 microliter aliquot portions. This is followed by 24 microliters of TMB substrate (i.e., a detector reagent) being aspirated from the TMB cup, and dispensed onto the slide at 4 microliter aliquot portions. Finally, blue color development of the spot of the matrix is recorded by optical reflectances (at 645 nanometers) for 60 seconds in preferably in one second intervals. The data is plotted, and the resulting linear curve fitted in Excel™ to obtain the kinetic read of the assay. The fPL progress curve and the fPL calibrated dose curve for this two-step protocol using the immunoassay test slide of the present invention are respectively shown in FIGS. 5 and 6 of the drawings.

A one-step protocol using the fPL immunoassay test slide of the present invention will now be described. In this one-step protocol, the sample and conjugate are mixed in the chemical analyzer's pipette tip beforehand and the mixture is then dispensed. An in-tip-mixing one-step protocol for testing a multiple of three fPL immunoassay slides is described below.

Typically, 80 microliters of sample are first aspirated from the sample cup into the pipette tip of the chemical analyzer. 80 microliters of conjugate are then aspirated from the conjugate cup into the analyzer's pipette tip containing the sample. The sample and conjugate are mixed inside the analyzer's pipette tip for 10 seconds with a tip-mix-volume of 10 microliters.

For a multiple premix dispensing protocol, 30 microliters of the sample/conjugate premix are dispensed onto the immunoassay test slides of the present invention at 10 microliter aliquot portions.

For a single premix dispensing protocol, 15 microliters of the sample/conjugate premix are dispensed onto the immunoassay test slides of the present invention at 15 microliter aliquot portions preferably with a 90 second post-premix dispense time delay. The post-premix dispense time delay is preferably provided to permit sufficient incubation time for the immuno-reaction on the slides.

Figure 7:
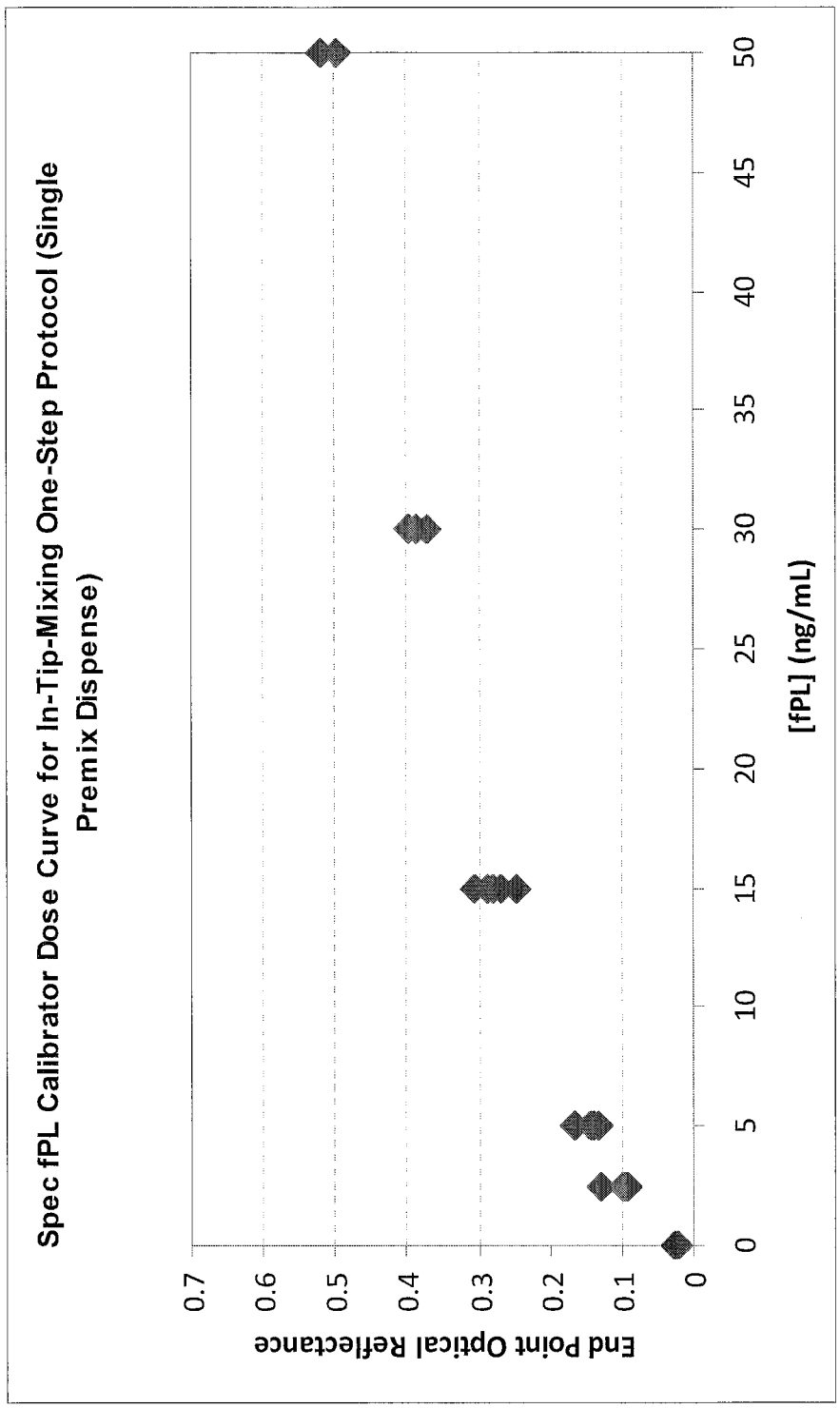
FIG. 7 is a graph of optical reflectance versus nanograms/milliliters showing the calibrator dose curve for a one-step test protocol (single premix dispense) using an fPL immunoassay test slide formed in accordance with the present invention.
Figure 8:
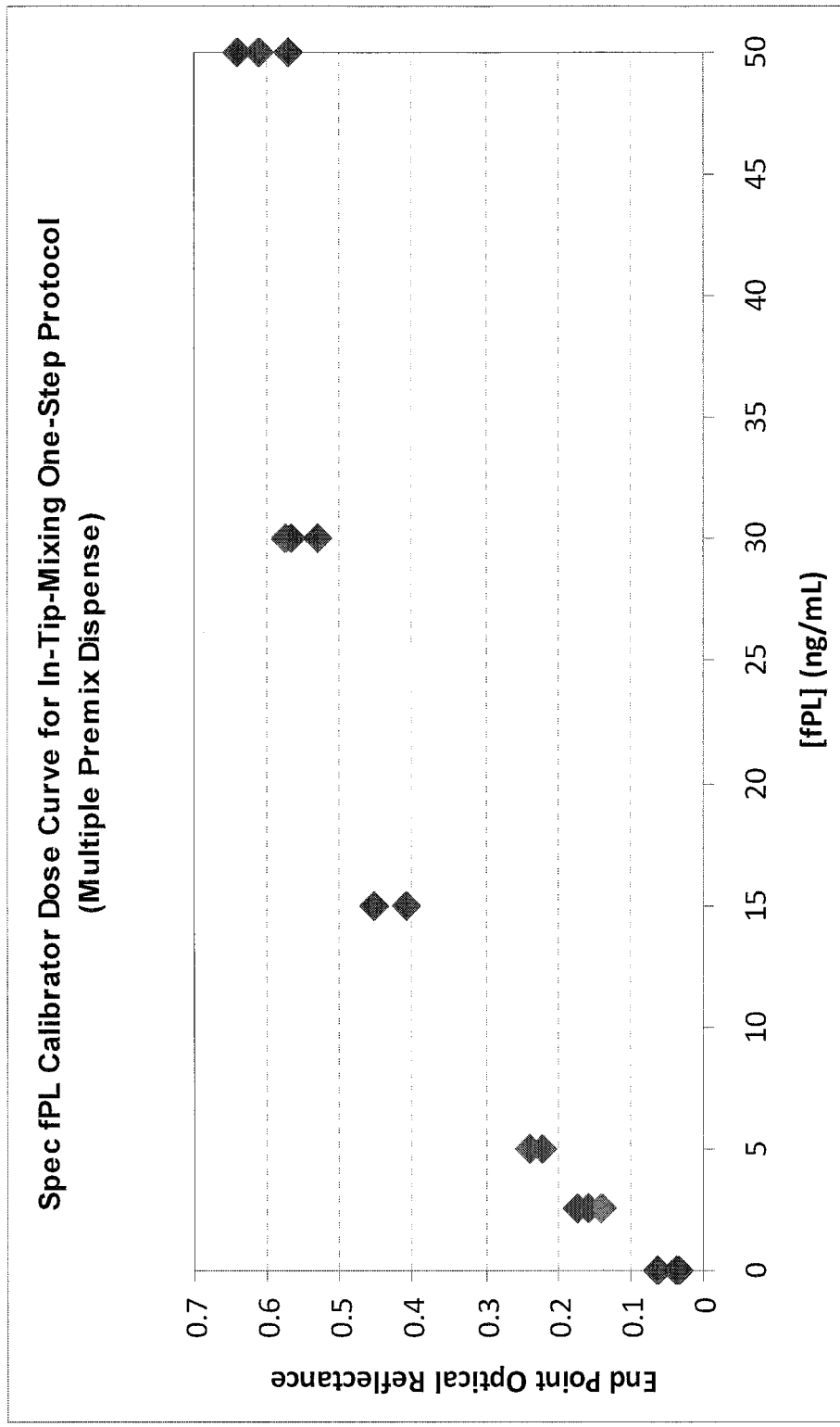
FIG. 8 is a graph of optical reflectance versus nanograms/milliliters showing the calibrator dose curve for a one-step test protocol (multiple premix dispense) using an fPL immunoassay test slide formed in accordance with the present invention.
Figure 9:
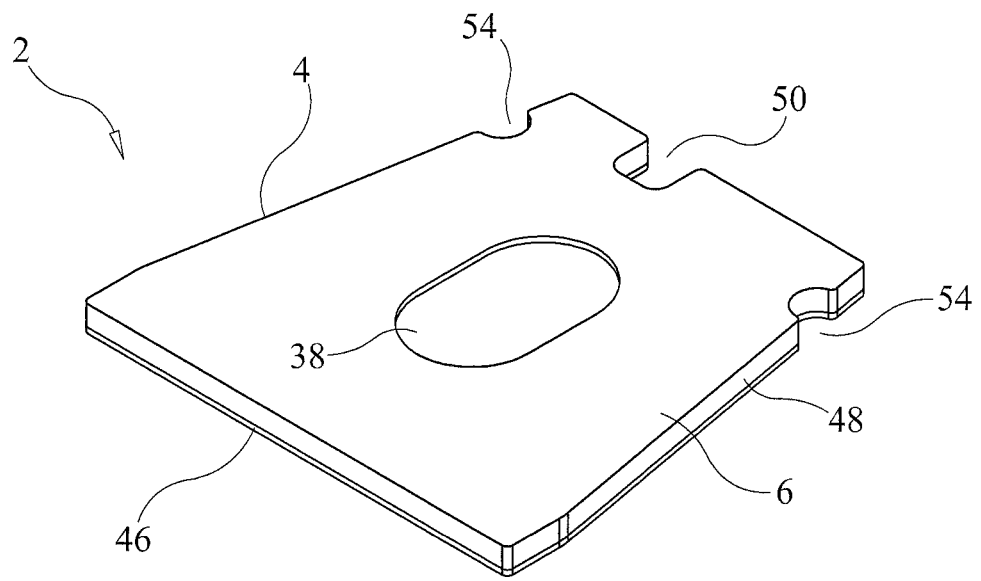
FIG. 9 is a top perspective view of a further embodiment of an immunoassay test slide formed in accordance with the present invention.

Then, 30 microliters of a wash buffer are dispensed onto the slides at 10 microliter aliquot portions. Following this, 12 microliters of the TMB substrate are dispensed onto the slides at 12 microliter aliquot portions. Finally, blue color development of the spot on the test slide matrix 12 is recorded by optical reflectance (OR) at 645 nanometers for 60 seconds in preferably two second intervals. The data are then plotted to obtain an end point read of the assay. For the in-tip-mixing one-step test protocol, the spec fPL calibrator dose curves corresponding to the single and multiple premix dispense are respectively shown in FIGS. 7 and 8 of the drawings.

The color change of the slide 2 detected by the reflectometer, or the fluorescence of the slide detected by the fluorometer, of the chemical analyzer may be measured quantitatively or qualitatively to determine the amount of analyte in the fluid sample (see FIG. 21B and Step 6 in FIG. 21A). It is envisioned that the immunoassay test slide 2 of the present invention may be loaded into the chemical analyzer with other immunoassay slides or with dry chemistry reagent test slides, the slides being tested concurrently. Another advantage of the immunoassay test slide over other conventional methods and devices for performing assays is the minute quantity of fluid sample and liquid reagents required for detecting the presence of an analyte in the fluid sample. In one conventional immunoassay test device commonly referred to by the trademark SNAP and manufactured by IDEXX Laboratories, Inc., approximately 1,330 microliters of sample and liquid reagents are typically required to perform the assay and obtain detectable results. However, with the immunoassay test slide 2 of the present invention, less than 100 microliters of sample and liquid reagents are required to perform an assay to obtain detectable results.

The immunoassay test slide 2 of the present invention may be formed by placing a die cut section of porous carrier matrix 12 from a sheet of the same material between a cover piece 6 and a bottom piece 8 of a plastic material, such as polystyrene, specifically shaped to be matable. The two pieces may be joined together by applying heat or an adhesive to define a substantially leakproof housing 4 in which resides the porous carrier matrix 12. The porous carrier matrix 12 may be spotted with an immobilized specific binding reagent prior to its insertion between the two mating slide pieces, or may be spotted with the specific binding reagent and heated to a specific temperature and for a predetermined period time to dry and immobilize the binding reagent in the central portion of the matrix 12. If a bottom opening 40, formed in the bottom piece 8 of the immunoassay test slide 2, is provided, then prior to the insertion of the porous carrier matrix 12 between the cover piece 6 and the bottom piece 8, a thin sheet of transparent (clear) material 42, such as Mylar, is preferably used and placed within the interior cavity 10 defined by the slide housing 4 over the bottom opening 40. Alternatively, no such bottom opening or covering sheet is required if the bottom piece 8 of the slide is formed from a light transmissible or transparent material, such as polystyrene.

Figure 2:
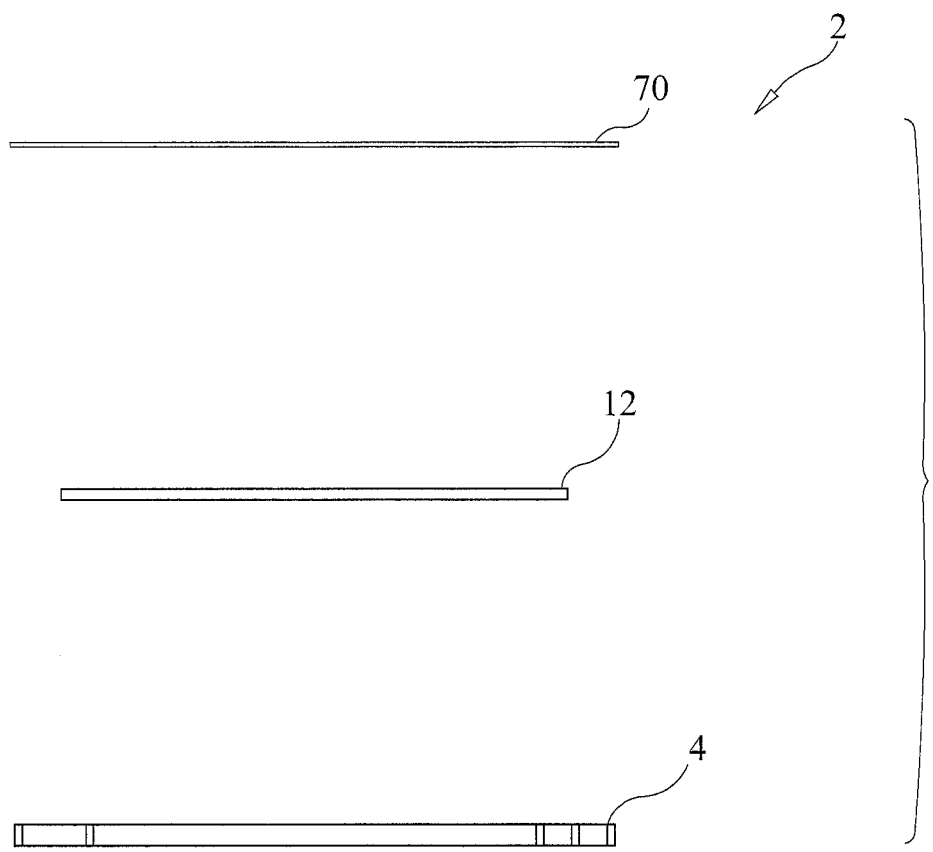
FIG. 2 is an exploded, side elevational view of the immunoassay test slide of the present invention shown in FIG. 1.
Figure 3:
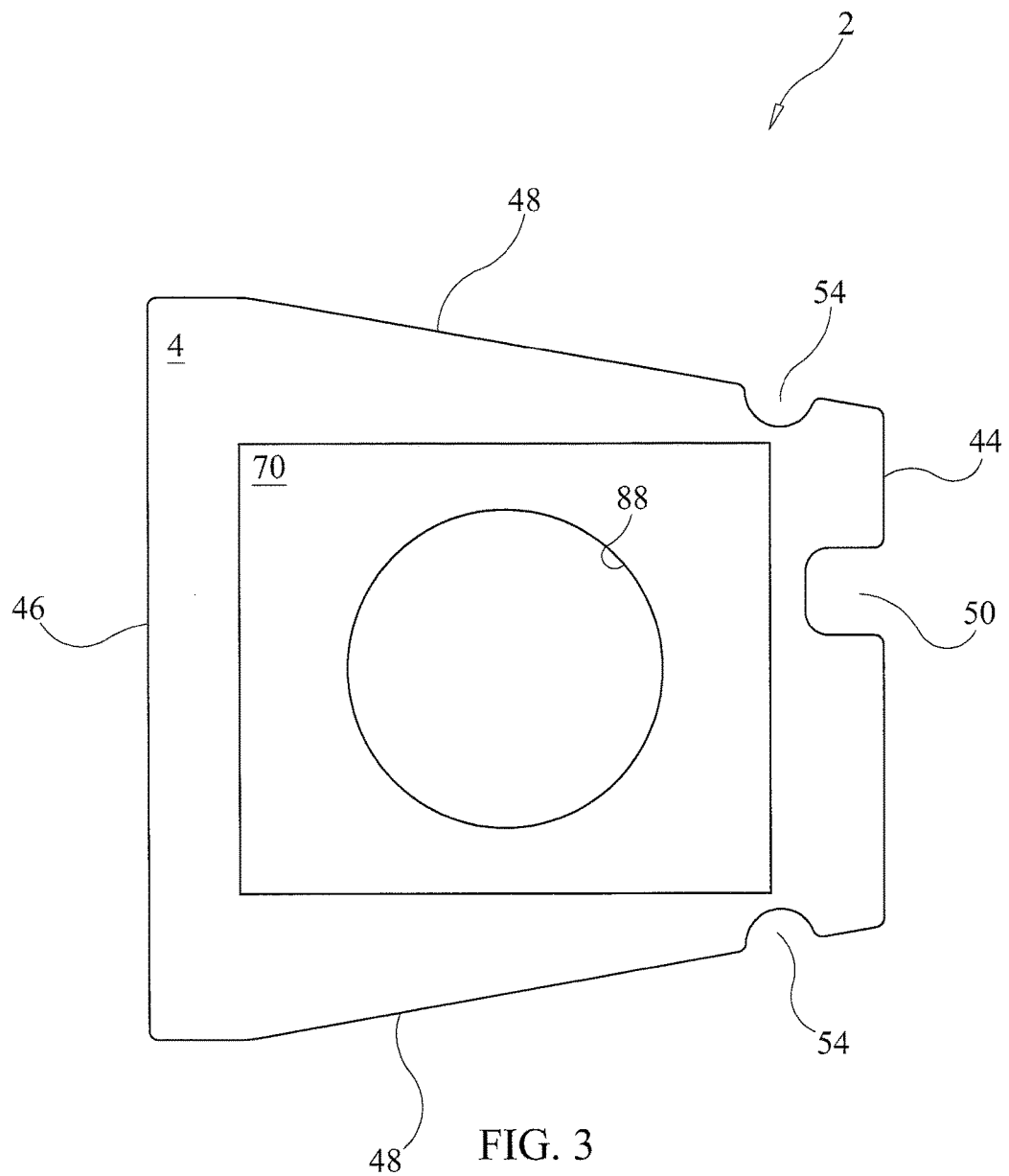
FIG. 3 is a top plan view of the immunoassay test slide of the present invention shown in FIG. 1.
Figure 4:
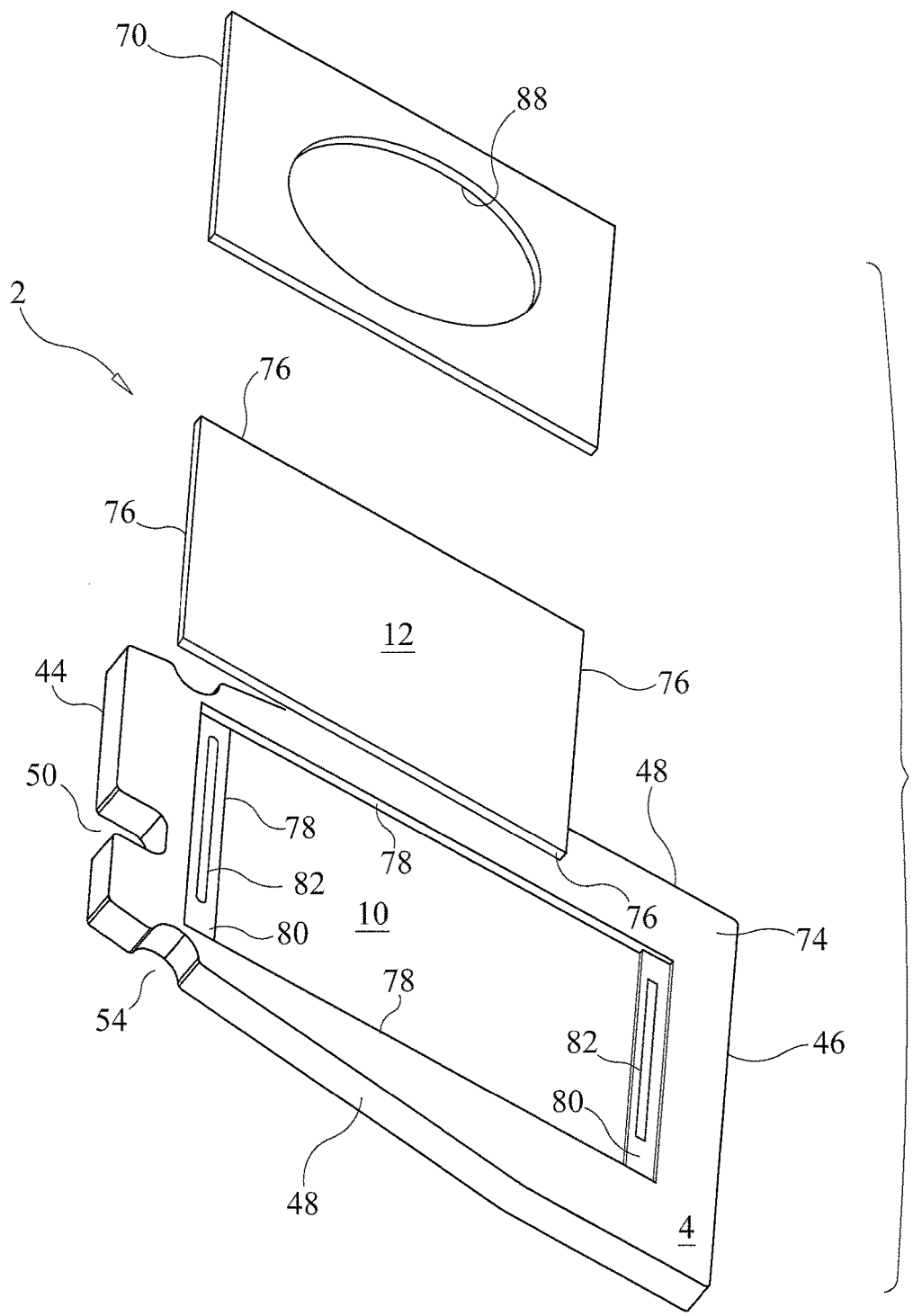
FIG. 4 is an exploded, top perspective view of yet another embodiment of the immunoassay test slide formed in accordance with the present invention.

Other embodiments of the immunoassay test slide 2 of the present invention are shown in FIGS. 1-4. Each of the test slides 2 of these further embodiments includes a slide housing 4, a porous carrier matrix or membrane 12, such as described previously, and a film or cover sheet 70. As shown in FIGS. 1-4, the slide housing 4 is preferably trapezoidal in overall shape, but may be rectangular or square. Thus, the slide housing includes a front wall 44, a rear wall 46 situated opposite the front wall, and two opposite lateral walls 48. If the immunoassay test slide housing 4 is rectangular in shape, than each wall 44-48 is perpendicularly joined to its next adjacent wall. If the immunoassay test slide housing has a trapezoidal shape, such as shown in FIGS. 1-4, then the front and rear walls 44, 46 are generally parallel to each other, and the rear wall 46 has a length which is greater than that of the front wall 44, and the opposite lateral walls 48 are non-parallel to each other and mutually converge from the rear wall 46 toward the front wall 44. The embodiment of the immunoassay test slide shown in FIG. 4 is similar in structure to that of the immunoassay test slide shown in FIGS. 1-3 except that the two opposite lateral walls 48 are longer than those of the test slide shown in FIGS. 1-3, giving the embodiment of the slide housing shown in FIG. 4 an elongated trapezoidal shape. As with the embodiments described previously, the immunoassay test slides 2 shown in FIGS. 1-4 may include an indexing notch 50 for proper orientation of the test slide on an analytical instrument, and lateral side recesses 54 used for loading the test slides on an analytical instrument, in the same manner and in the same locations as the notch and lateral side recesses included in the dry chemistry test slides disclosed in the aforementioned Heidt, et al. patent and the Rich, et al. published application.

In the embodiments of the immunoassay test slides of the present invention shown in FIGS. 1-4, the test slide housing 4 includes a recessed portion 72 of the top side 74 thereof to define a recess or cavity 10 which may be square, rectangular or even trapezoidal in shape. This cavity 10 is dimensioned to at least partially receive therein the porous carrier matrix 12. The matrix 12 performs the same function and may be made from the same material as the matrix described previously with respect to the other embodiments of the immunoassay test slide, that is, for holding a specific binding reagent and for absorbing a predetermined volume of fluid sample and conjugate reagent. Furthermore, the porous carrier matrix 12 is formed in the same manner as described previously with the other embodiments of the immunoassay test slide, and is preferably dimensioned to be slightly smaller than the dimensions of the cavity 10 formed in the slide housing 4 so that its lateral edges 76 are spaced slightly away from the interior side walls 78 of the slide housing 4 defining the cavity 10 so as to define a channel or well 62 between the matrix 12 and the interior side walls 78 at least partially about the periphery of the housing. As with the other embodiments, this channel or well 62 is provided to receive any overflow of fluid sample, reagent or wash solution from the matrix 12 which is envisioned to become saturated with such fluids. The well or channel 62 provides capacity in excess of the volume of fluid sample, reagents and wash solutions saturating the porous matrix 12. The preferred volume of the cavity 10 defined by the recessed portion 72 of the housing 4 is the same as that described previously with respect to the other embodiments of the immunoassay test slides.

The preferred material from which the porous matrix 12 is formed is referred to by the trademark Fusion 5™ available from Whatman, Inc., USA, which is a glass fiber-based material that contains a plastic binder.

Figure 10:
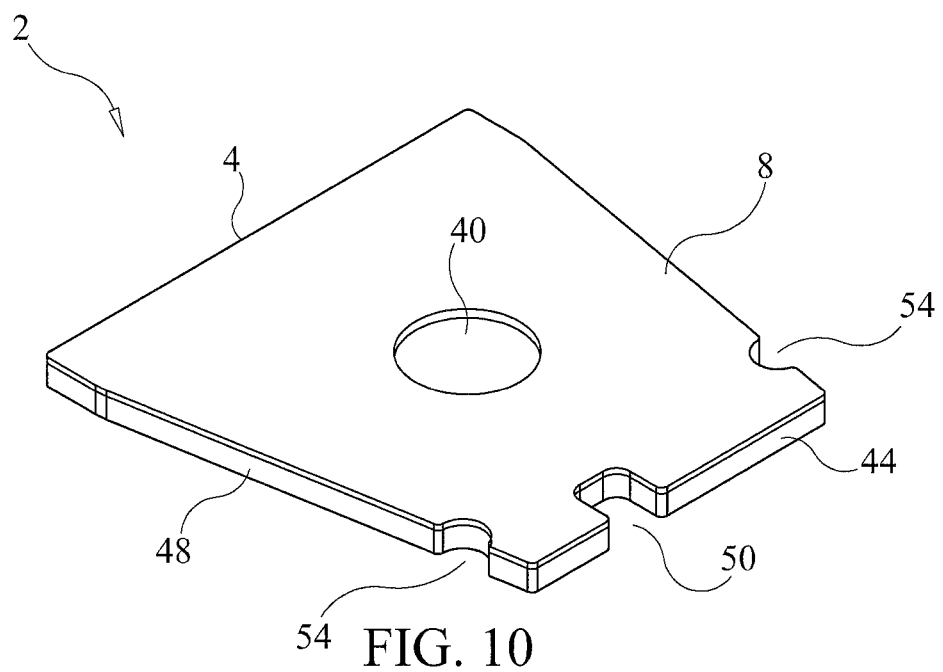
FIG. 10 is a bottom perspective view of the immunoassay test slide of the present invention shown in FIG. 9.
Figure 11:
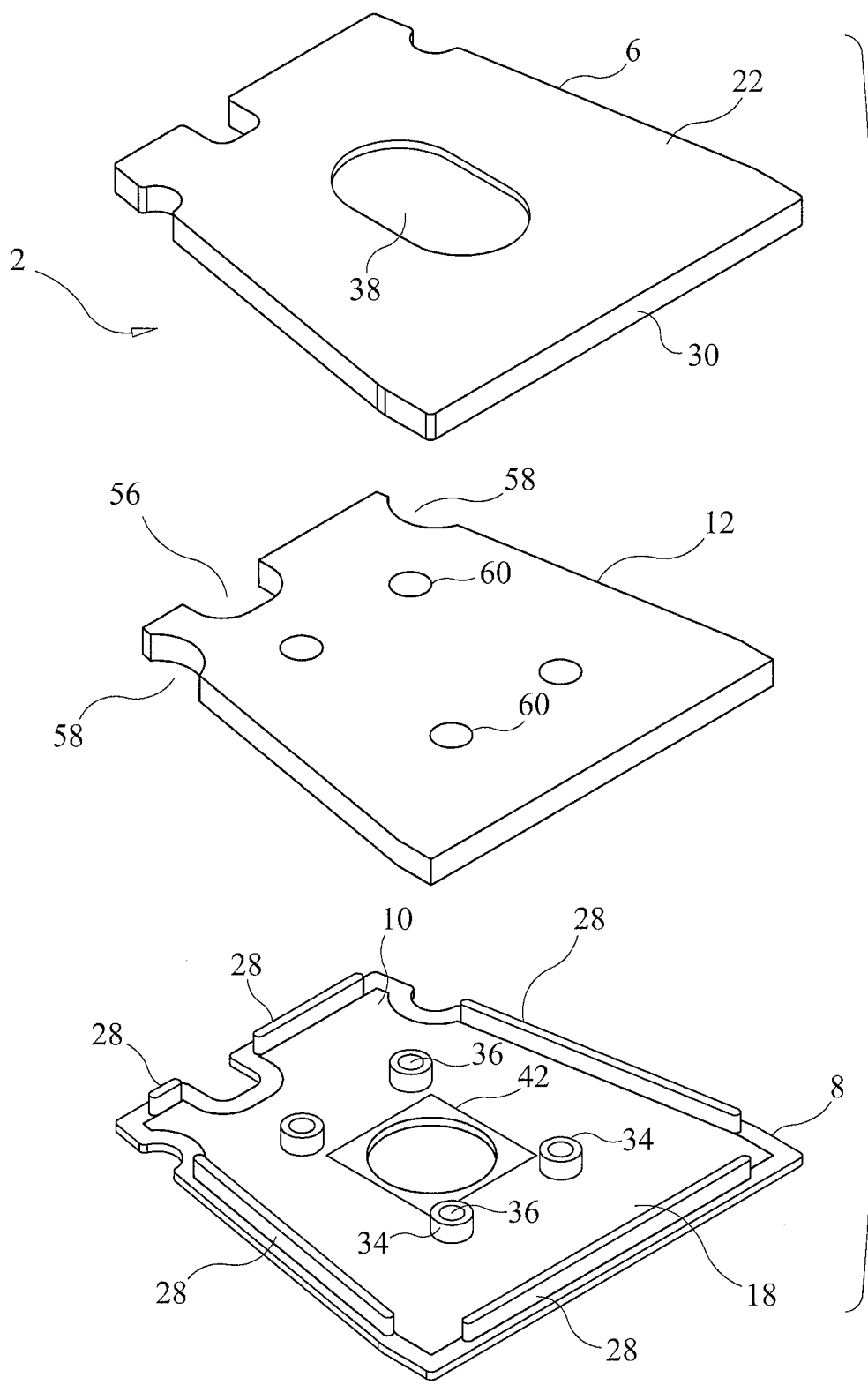
FIG. 11 is an exploded, top perspective view of the immunoassay test slide of the present invention shown in FIGS. 9 and 10.

Preferably, the slide housing 4 is formed from crystal polystyrene, although it may be formed from the same materials which were described previously with respect to the other embodiments of the immunoassay test slide. The crystal polystyrene is transparent or at least translucent. However, it is envisioned that a bottom opening 40, such as shown in FIG. 10, may be formed through the bottom side of the housing 4 if the housing is formed from a less light transmissive or opaque material. Then, a transparent or clear (light transmissive) thin sheet of material 42 (see FIG. 11), such as a Mylar film, may be placed over the bottom opening and adhesively joined or heat sealed to the inner surface of the bottom side in alignment with the recess or cavity 10 of the slide housing, that is, interposed between the inner surface of the bottom side of the housing and the absorbent porous material 12, to insure the leakproofness of the housing 4. The crystal styrene material from which the slide housing 4 is preferably formed allows visible or infrared light, and more preferably, light at a wavelength of about 645 nanometers, to permeate therethrough. Thus, light emitted by the reflectometer 684 or fluorometer 652 of the analytical instrument will pass through the transparent bottom side of the slide housing 4 when the analytical instrument is conducting reflectance or fluorescence measurements on the immunoassay test slide.

Preferably, a recessed ledge 80, raised above the floor of the recessed portion 72 that receives the matrix 12 but slightly below the surface of the top side 74 of the slide housing, is formed on at least two opposite sides of the recess or cavity 10. Preferably, each ledge 80 includes an elongated rib 82 which protrudes slightly above and outwardly from the top surface of the ledge 80. As will be seen, the elongated ribs 82 are used as "energy directors" and are provided for welding purposes. The ribs 82 bond to the flat underside surface of the covering film 70 to affix the covering film 70 to the slide housing 4 thereby securing the matrix 12 within the recess 10 under the film covering when the slide is being assembled. Furthermore, the top side 74 of the slide housing may include a bar code 86 situated thereon to identify the type of reagent used on the slide, which bar code 86 is read by an optical code reader forming part of the chemical analyzer.

A thin polystyrene film 70 is placed over the porous matrix 12 and preferably resides in or above the recess or cavity 10 formed in the top side 74 of the slide housing 4. Preferably, this polystyrene film 70 has a thickness of about 0.2 millimeters. The film 70 is preferably dimensioned to closely fit within the recess 10 in which the energy directors or ribs 82 reside, the opposite interior side walls 78 of the slide housing 10 being situated and dimensioned to help position the covering film 70 therebetween.

The polystyrene covering film 70 includes an opening 88 formed through the thickness thereof, in much the same way as the cover piece 6 of the immunoassay test slides described previously has an opening 38. The top opening 88 is provided so that a precise amount of a sample fluid, such as blood, serum and the like, and reagents may be metered onto the test slide 2 and deposited on the porous matrix 12 situated under the opening 88, by a sample metering device 84 of the dry chemistry analytical instrument such as disclosed in the aforementioned Heidt et al. '229 patent and the Rich, et al. published application. This top opening 88 may be circular, as shown in FIGS. 1-3, rectangular, or oval or elongated in shape, as shown in FIG. 4. Preferably, the opening 88 formed through the top film portion 70 has a width along a minor axis thereof of between about 6 millimeters and about 12 millimeters, and more preferably about 10 millimeters, if the opening is oblong in shape, and has a diameter of between about 6 millimeters and about 12 millimeters, and more preferably about 10 millimeters, if the opening is circular in shape. The covering film 70 is situated on the test slide housing 4 by closely positioning the covering film within the recess 10 defined by the lateral walls 78 of the housing so that the film 70 completely covers the porous matrix 12 situated within the recess or cavity 10 of the slide housing. The covering film 70 may be joined to the slide housing 4 by an adhesive, or by sonic welding or heat stamping the film to the housing. Even more preferably, the underside surface of the film 70 rests on the ledges 80 and contacts the energy directors or ribs 82, and the film 70 is joined to the ledges 80 by sonic welding using the energy directors 82.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An immunoassay test slide, which comprises:
    a housing, the housing having a top side and a bottom side, a front side, a rear side situated opposite the front side, and opposite lateral sides, the housing defining a cavity; and
    a fluid flow matrix, the fluid flow matrix being disposed within the cavity of the housing for receiving a fluid sample containing an analyte, or one or more liquid reagents;
    wherein the housing is formed with one of a rectangular shape and a trapezoidal shape;
    wherein the bottom side of the housing is formed from a light transmissive material;
    wherein the top side of the housing includes a recessed portion to at least partially define the cavity for receiving the fluid flow matrix;
    wherein the cavity is situated between the front and rear sides and between the opposite lateral sides of the housing;
    wherein the test slide further comprises:
    a top film portion, the top film portion being situated on the housing opposite the bottom side and in alignment with and covering the fluid flow matrix, the top film portion having an opening formed through the thickness thereof which is in communication with the cavity of the housing and which is provided to receive the fluid sample containing an analyte or the one or more liquid reagents, the fluid flow matrix being disposed within the housing and situated in alignment with the top opening formed in the film portion to receive thereon the fluid sample or the one or more liquid reagents; and
    wherein the fluid flow matrix is formed from a glass fiber-based material that contains a plastic binder.

2. An immunoassay test slide as defined by claim 1, wherein the top side of the housing includes at least one recessed ledge, the at least one recessed ledge being situated adjacent to the recessed portion which receives the fluid flow matrix, the at least one recessed ledge having a top surface on which a portion of the underside surface of the top film portion rests.

3. An immunoassay test slide as defined by claim 1, wherein the housing has a generally trapezoidal shape, and wherein the front and rear sides of the housing are generally parallel to each other and the rear side is longer than the front side.

4. An immunoassay test slide as defined by claim 1, wherein the top film portion is formed from a polystyrene material.

5. An immunoassay test slide as defined by claim 1, wherein the top film portion has a thickness of about 0.2 millimeters.

6. An immunoassay test slide as defined by claim 1, wherein the opening formed through the top film portion is one of circular or oblong.

7. An immunoassay test slide as defined by claim 6, wherein the opening formed through the top film portion has a width along a minor axis thereof of between about 6 millimeters and about 12 millimeters if the opening is oblong in shape, and has a diameter of between about 6 millimeters and about 12 millimeters if the opening is circular in shape.

8. An immunoassay test slide as defined by claim 7, wherein the opening formed through the top film portion has a width along a minor axis thereof of about 10 millimeters if the opening is oblong in shape, and has a diameter of about 10 millimeters if the opening is circular in shape.

9. An immunoassay test slide as defined by claim 1, wherein the slide housing is formed from a polystyrene material.

10. An immunoassay test slide as defined by claim 1, wherein the top side of the slide housing includes a bar code situated thereon.

11. An immunoassay test slide as defined by claim 1, which further comprises:
    at least one immobilized analyte capture reagent situated on the fluid flow matrix in alignment with the top opening in the top film portion.

12. An immunoassay test slide as defined by claim 1, wherein the front side of the housing has formed therein an orientation notch.

13. An immunoassay test slide as defined by claim 1, wherein each lateral side of the housing has formed therein a recess.

14. An immunoassay test slide as defined by claim 1, wherein the cavity of the housing has a volume of from about 20 microliters to about 200 microliters.

15. The immunoassay device of claim 1, wherein the fluid flow matrix is treated with a surfactant.

16. The immunoassay device of claim 1, wherein the bottom side of the housing is fabricated from a material that can be permeated by visible or infrared light.

17. The immunoassay device of claim 16, wherein the bottom side of the housing is fabricated from a material that can be permeated by light having a wavelength of 645 nanometers.

18. The immunoassay device of claim 1, further comprising an antibody or antigen disposed on the fluid flow matrix.

19. The immunoassay device of claim 1, wherein the fluid flow matrix has a volume that occupies at least about 50% of the cavity of the housing.

20. The immunoassay device of claim 1, wherein the fluid flow matrix has a volume that occupies at least about 60% of the cavity of the housing.

21. The immunoassay device of claim 1, wherein the fluid flow matrix has a volume that occupies at least about 70% of the cavity of the housing.

22. The immunoassay device of claim 1, wherein the fluid flow matrix has a volume that occupies at least about 80% of the cavity of the housing.

23. The immunoassay device of claim 1, wherein the fluid flow matrix has a volume that occupies at least about 90% of the cavity of the housing.

24. An immunoassay test slide, which comprises:
a housing, the housing having a top side and a bottom side, a front side, a rear side situated opposite the front side, and opposite lateral sides, the housing defining a cavity; and
a fluid flow matrix, the fluid flow matrix being disposed within the cavity of the housing for receiving a fluid sample containing an analyte, or one or more liquid reagents;
wherein the housing is formed with one of a rectangular shape and a trapezoidal shape;
wherein the bottom side of the housing is formed from a light transmissive material;
wherein the top side of the housing includes a recessed portion to at least partially define the cavity for receiving the fluid flow matrix;
wherein the cavity is situated between the front and rear sides and between the opposite lateral sides of the housing;
wherein the test slide further comprises:
a top film portion, the top film portion being situated on the housing opposite the bottom side and in alignment with and covering the fluid flow matrix, the top film portion having an opening formed through the thickness thereof which is in communication with the cavity of the housing and which is provided to receive the fluid sample containing an analyte or the one or more liquid reagents, the fluid flow matrix being disposed within the housing and situated in alignment with the top opening formed in the film portion to receive thereon the fluid sample or the one or more liquid reagents; and
wherein the housing further includes a side wall surrounding the cavity, at least a portion of the side wall being spaced laterally from the fluid flow matrix to define therebetween a channel for receiving an excess volume of the fluid sample or the one or more liquid reagents.

25. An immunoassay test slide as defined by claim 24, wherein the top side of the housing includes at least one recessed ledge, the at least one recessed ledge being situated adjacent to the recessed portion which receives the fluid flow matrix, the at least one recessed ledge having a top surface on which a portion of the underside surface of the top film portion rests.

26. An immunoassay test slide as defined by claim 24, wherein the housing has a generally trapezoidal shape, and wherein the front and rear sides of the housing are generally parallel to each other and the rear side is longer than the front side.

27. An immunoassay test slide as defined by claim 24, wherein the top film portion is formed from a polystyrene material.

28. An immunoassay test slide as defined by claim 24, wherein the top film portion has a thickness of about 0.2 millimeters.

29. An immunoassay test slide as defined by claim 24, wherein the opening formed through the top film portion is one of circular or oblong.

30. An immunoassay test slide as defined by claim 29, wherein the opening formed through the top film portion has a width along a minor axis thereof of between about 6 millimeters and about 12 millimeters if the opening is oblong in shape, and has a diameter of between about 6 millimeters and about 12 millimeters if the opening is circular in shape.

31. An immunoassay test slide as defined by claim 29, wherein the opening formed through the top film portion has a width along a minor axis thereof of about 10 millimeters if the opening is oblong in shape, and has a diameter of about 10 millimeters if the opening is circular in shape.

32. An immunoassay test slide as defined by claim 24, wherein the slide housing is formed from a polystyrene material.

33. An immunoassay test slide as defined by claim 24, wherein the top side of the slide housing includes a bar code situated thereon.

34. An immunoassay test slide as defined by claim 24, which further comprises:
at least one immobilized analyte capture reagent situated on the fluid flow matrix in alignment with the top opening in the top film portion.

35. An immunoassay test slide as defined by claim 24, wherein the front side of the housing has formed therein an orientation notch.

36. An immunoassay test slide as defined by claim 24, wherein each lateral side of the housing has formed therein a recess.

37. An immunoassay test slide as defined by claim 24, wherein the cavity of the housing has a volume of from about 20 microliters to about 200 microliters.

38. The immunoassay device of claim 24, wherein the fluid flow matrix is treated with a surfactant.

39. The immunoassay device of claim 24, wherein the bottom side of the housing is fabricated from a material that can be permeated by visible or infrared light.

40. The immunoassay device of claim 39, wherein the bottom side of the housing is fabricated from a material that can be permeated by light having a wavelength of 645 nanometers.

41. The immunoassay device of claim 24, further comprising an antibody or antigen disposed on the fluid flow matrix.

42. The immunoassay device of claim 24, wherein the fluid flow matrix has a volume that occupies at least about 50% of the cavity of the housing.

43. The immunoassay device of claim 24, wherein the fluid flow matrix has a volume that occupies at least about 60% of the cavity of the housing.

44. The immunoassay device of claim 24, wherein the fluid flow matrix has a volume that occupies at least about 70% of the cavity of the housing.

45. The immunoassay device of claim 24, wherein the fluid flow matrix has a volume that occupies at least about 80% of the cavity of the housing.

46. The immunoassay device of claim 24, wherein the fluid flow matrix has a volume that occupies at least about 90% of the cavity of the housing.

47. An immunoassay test slide as defined by claim 24, wherein the fluid flow matrix is formed from a porous material selected from the group consisting of natural, synthetic, or naturally occurring or synthetically modified materials; fibrous materials; membranes of cellulose materials, including paper, cellulose, and cellulose derivatives, including cellulose acetate and nitrocellulose, fiberglass, glass fiber, cloth, both naturally occurring, including cotton, and synthetic, including nylon; porous gels, including silica gel, agarose, dextran and gelatin; porous fibrous matrices; starch based materials; cross-linked dextran chains; ceramic materials; olefin and thermoplastic materials, including films of polyvinyl chloride, polyethylene, polyvinyl acetate, polyamide, polycarbonate, polystyrene, copolymers of vinyl acetate and vinyl chloride and combinations of polyvinyl chloride-silica.

* * * * *